US008858807B2

(12) United States Patent
DeVoe et al.

(10) Patent No.: US 8,858,807 B2
(45) Date of Patent: Oct. 14, 2014

(54) PROCESS FOR MAKING MICRONEEDLES, MICRONEEDLE ARRAYS, MASTERS, AND REPLICATION TOOLS

(75) Inventors: Robert J. DeVoe, Minneapolis, MN (US); Dennis E. Ferguson, Mahtomedi, MN (US); Franklyn L. Frederickson, Esko, MN (US); Mitchell A. F. Johnson, Maplewood, MN (US); Mikhail L. Pekurovsky, Bloomington, MN (US); Craig R. Sykora, New Richmond, WI (US); Jeremy K. Larsen, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 896 days.

(21) Appl. No.: 12/293,012

(22) PCT Filed: Mar. 23, 2007

(86) PCT No.: PCT/US2007/064789
§ 371 (c)(1),
(2), (4) Date: Sep. 15, 2008

(87) PCT Pub. No.: WO2007/112309
PCT Pub. Date: Oct. 4, 2007

(65) Prior Publication Data
US 2009/0099537 A1    Apr. 16, 2009

Related U.S. Application Data

(60) Provisional application No. 60/785,656, filed on Mar. 24, 2006.

(51) Int. Cl.
*B44C 1/22* (2006.01)
*C08F 2/50* (2006.01)
*A61M 37/00* (2006.01)

(52) U.S. Cl.
CPC ... *A61M 37/0015* (2013.01); *A61M 2037/0053* (2013.01); *A61M 2037/0046* (2013.01); *A61M 2037/0038* (2013.01); *C08F 2/50* (2013.01)
USPC ................. 216/11; 216/2; 604/272

(58) Field of Classification Search
CPC ............... A61M 37/0015; A61M 2037/0053; A61M 2037/0023; A61M 2037/0046; A61K 9/0021
USPC ............................. 216/2, 11; 604/21, 22, 272
See application file for complete search history.

(56) References Cited

U.S. PATENT DOCUMENTS

| 3,018,262 A | 1/1962 | Schroeder |
|---|---|---|
| 3,729,313 A | 4/1973 | Smith |

(Continued)

FOREIGN PATENT DOCUMENTS

| WO | 98/21521 | 5/1998 |
|---|---|---|
| WO | 99/53242 | 10/1999 |
| WO | 2005/082596 | 9/2005 |

OTHER PUBLICATIONS

ASTM D1238, "Standard Test Method for Melt Flow Rates of Thermoplastics by extrusion Plastometer", Dec. 2004.

(Continued)

*Primary Examiner* — Roberts Culbert

(57) ABSTRACT

A process for making a microneedle array master comprises: (a) providing a photoreactive composition, the photoreactive composition comprising: (1) at least one reactive species that is capable of undergoing an acid- or radical-initiated chemical reaction, and (2) at least one multiphoton photoinitiator system; and (b) imagewise exposing at least a portion of the composition to light sufficient to cause simultaneous absorption of at least two photons, thereby inducing at least one acid- or radical-initiated chemical reaction where the composition is exposed to the light, the imagewise exposing being carried out in a pattern that is effective to define at least the surface of a plurality of microneedles. The microneedles may be solid and the outer surface of the microneedles may be characterized by at least one concave area. The master may be used to fabricate a tool for replication.

20 Claims, 9 Drawing Sheets

(56) References Cited

U.S. PATENT DOCUMENTS

| | | |
|---|---|---|
| 3,741,769 A | 6/1973 | Smith |
| 3,779,778 A | 12/1973 | Smith et al. |
| 3,808,006 A | 4/1974 | Smith |
| 4,250,053 A | 2/1981 | Smith |
| 4,279,717 A | 7/1981 | Eckberg et al. |
| 4,394,403 A | 7/1983 | Smith |
| 4,489,033 A | 12/1984 | Uda et al. |
| 4,491,628 A | 1/1985 | Ito et al. |
| 4,515,543 A | 5/1985 | Hammer |
| 4,642,126 A | 2/1987 | Zador et al. |
| 4,652,274 A | 3/1987 | Boettcher et al. |
| 4,859,572 A | 8/1989 | Farid et al. |
| 5,235,015 A | 8/1993 | Ali et al. |
| 5,376,317 A | 12/1994 | Maus et al. |
| 5,545,676 A | 8/1996 | Palazzotto et al. |
| 5,753,346 A | 5/1998 | Leir et al. |
| 5,770,737 A | 6/1998 | Reinhardt et al. |
| 5,856,373 A | 1/1999 | Kaisaki et al. |
| 5,859,251 A | 1/1999 | Reinhardt et al. |
| 5,998,495 A | 12/1999 | Oxman et al. |
| 6,025,406 A | 2/2000 | Oxman et al. |
| 6,100,405 A | 8/2000 | Reinhardt et al. |
| 6,248,281 B1 | 6/2001 | Abe et al. |
| 6,312,612 B1 | 11/2001 | Sherman et al. |
| 6,335,149 B1 | 1/2002 | Xu et al. |
| 6,379,324 B1 | 4/2002 | Gartstein et al. |
| 6,451,240 B1 * | 9/2002 | Sherman et al. .............. 264/504 |
| 6,852,766 B1 | 2/2005 | DeVoe |
| 6,855,478 B2 | 2/2005 | Devoe et al. |
| 6,924,087 B2 | 8/2005 | Yeshurun et al. |
| 2003/0045837 A1 | 3/2003 | Delmore et al. |
| 2004/0186419 A1 | 9/2004 | Cho |
| 2004/0267205 A1 * | 12/2004 | Stemme et al. .............. 604/173 |
| 2005/0261631 A1 | 11/2005 | Clarke et al. |
| 2008/0088066 A1 | 4/2008 | Ferguson et al. |
| 2008/0319404 A1 | 12/2008 | Pekurovsky et al. |

OTHER PUBLICATIONS

ASTM D638, "Standard Test Method for Tensile Properties of Plastics", May 2008.

ASTM D256, "Standard Test Methods for Determining the Izod Pendulum Impact Resistance of Plastics", Dec. 2006.

Handbook of Epoxy Resins, Lee and Neville, McGraw-Hill Book co., New York (1967).

R.D. Allen et al. "High Performance Acrylic Polymers for Chemically Amplified Photoresist Applications," J. Vac Sci. Technol. B. 9, 3357 (1991).

R.D. Allen et al. in Proc. SPIE 2438, 193 NM "Single Layer Resists Building Etch Resistance Into a High Resolution Imaging System," 474-485 (1995).

W. Zhou etr al. in Science 296, 1106-1109, An Efficient Two-Photon-Generated Photoacid Applied to Positive-Tone 3D Microfabrication, (2002).

C. Xu and W.W. Webb in J. Opt. Soc. Am B, 13, 481, "Measurement to Two-Photon Excitation Cross Sections of Molecular Fluorophores with Data from 690 to 1050 nm," (1996).

R.J. Cox, Photographic Sensitiviy, Chapter 15, Academic Press (1973).

N.L. Weinburg, Ed., Technique of Electroorganic Synthesis Part II Techniques of Chemistry, vol. V (1975).

C.K. Mann and K.K. Barnes, Electrochemical Reactions in Nonaqueous Systems (1970).

D.F. Eaton in Advances in Photochemistry, edited by B. Voman et al., vol. 13, pp. 427-487, "Dye Sensitized Photopolymerization" John Wiley and Sons, New York (1986).

Beringer et al., J.Am. Chem. Soc. 81, 342-351, "Diaryliodonium Salts, IX, the Synthesis of Substituted Diphenyliodonium Salts", (1959).

* cited by examiner

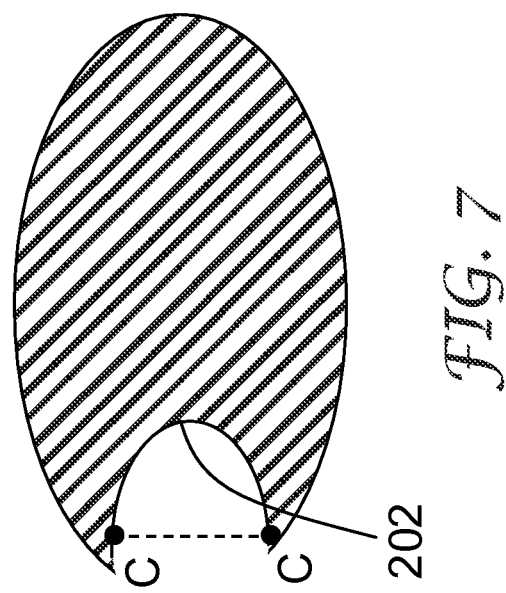
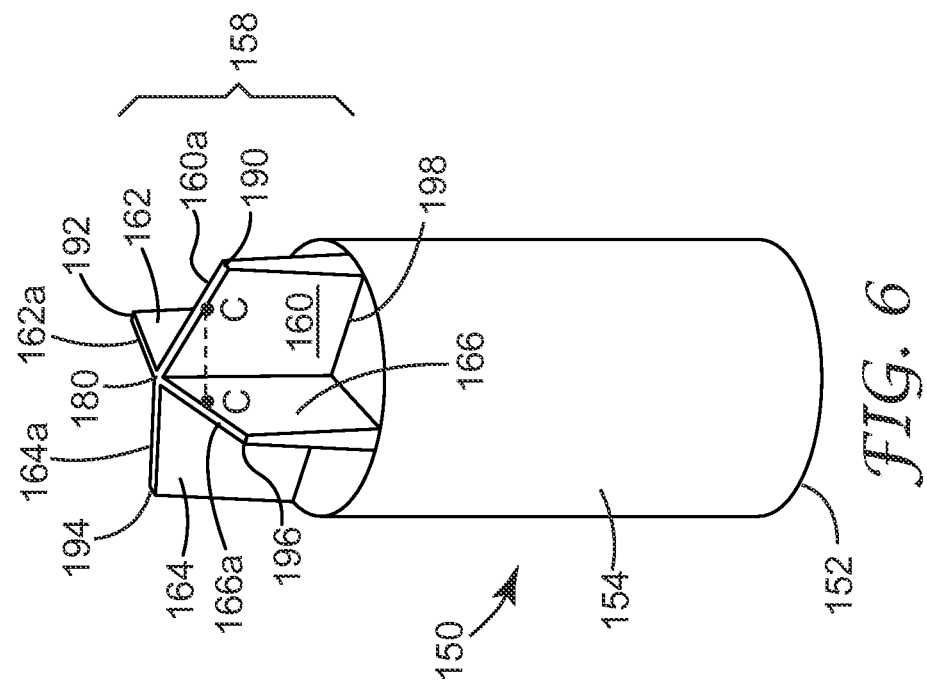

PROCESS FOR MAKING MICRONEEDLES, MICRONEEDLE ARRAYS, MASTERS, AND REPLICATION TOOLS

CROSS REFERENCE TO RELATED APPLICATIONS

This application is a national stage filing under 35 U.S.C. 371 of PCT/US2007/064789, filed Mar. 23, 2007, which claims priority to U.S. Provisional Application No. 60/785,656, filed Mar. 24, 2006, the disclosure of which is incorporated by reference in its/their entirety herein.

FIELD

This invention relates to processes for making microneedles, microneedle arrays, microneedle array masters and/or replication tools suitable for molding microneedles or microneedle arrays, and, in other aspects, to microneedles, microneedle arrays, microneedle array masters and/or replication tools suitable for molding microneedles made thereby.

BACKGROUND

Only a limited number of molecules with demonstrated therapeutic value can be transported through the skin via unassisted or passive transdermal drug delivery. The main barrier to transport of molecules through the skin is the stratum corneum (i.e., the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in order to pierce the stratum corneum such that the therapeutic agents and other substances can pass through that layer and into the tissues below.

A number of processes have been proposed for preparing microneedles and microneedle arrays. These processes include direct methods, that is, methods where a microneedle or microneedle array is directly fabricated, such as use of photolithography to prepare silicon microneedles. These processes also include indirect methods, that is, methods where a replication tool (e.g., a mold) is first prepared having the negative image of a microneedle or microneedle array and a microneedle or microneedle array is molded against the replication tool. However, microneedles are very fine structures that can be difficult to prepare in a precise and cost-effective manner.

SUMMARY

Thus, we recognized that there is a need for processes that can be used to fabricate microneedle arrays that can meet the quality, cost, and/or performance requirements of a variety of different applications. In particular, we recognize a need for processes that are capable of producing microneedle arrays with complex outer surfaces, such as those characterized by at least one concave area.

Briefly, in one aspect, this invention provides a process comprising
  (a) providing a photoreactive composition, said photoreactive composition comprising
    (1) at least one reactive species that is capable of undergoing an acid- or radical-initiated chemical reaction, and
    (2) at least one multiphoton photoinitiator system; and
  (b) imagewise exposing at least a portion of said composition to light sufficient to cause simultaneous absorption of at least two photons, thereby inducing at least one acid- or radical-initiated chemical reaction where said composition is exposed to the light, said imagewise exposing being carried out in a pattern that is effective to define at least the surface of a plurality of solid microneedles, wherein the outer surface of the microneedles is characterized by at least one concave area.

It has been discovered that multiphoton photofabrication processes can be well-suited for fabricating microneedle arrays, particularly arrays where the microneedles have a complex outer surface shape.

The process of the invention involves the use of relatively low-cost materials (for example, polymers). The process also enables cost-effective replication (for example, through the production of masters). Furthermore, the process is capable of flexibly and controllably producing microneedles of various different shapes and heights (that is, different profiles) and microneedle arrays of various different symmetries and arrangements.

Thus, at least some embodiments of the process of the invention meet the above-stated need for microneedle array fabrication processes that can satisfy the quality, cost, and/or performance requirements of a variety of different applications. Microneedle arrays made by the process of the invention can be suitable for use in numerous applications including, for example, in providing vaccinations or delivering macromolecules across the stratum corneum.

BRIEF DESCRIPTION OF DRAWING

These and other features, aspects, and advantages of the present invention will become better understood with regard to the following description, appended claims, and accompanying drawings, wherein:

FIG. 6 is a schematic perspective view of still another microneedle.

FIG. 7 is a schematic cross-sectional view of still another microneedle.

DETAILED DESCRIPTION

Definitions

Figure 1:
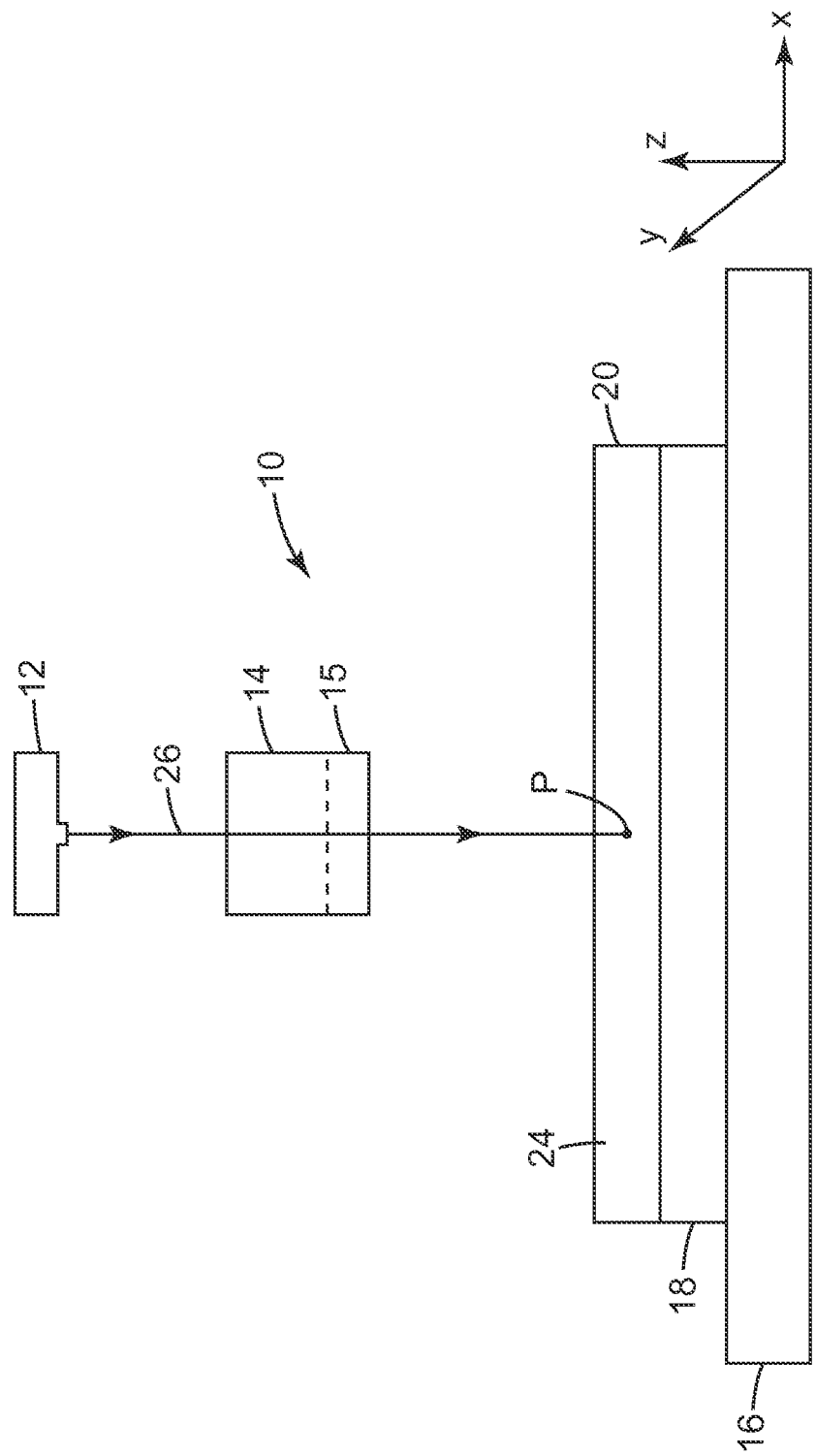
FIG. 1 is a schematic representation of an exemplary multiphoton photofabrication system useful for carrying out the process of the invention.

As used in this patent application:

"cure" means to effect polymerization and/or to effect crosslinking;

"electronic excited state" means an electronic state of a molecule that is higher in energy than the molecule's electronic ground state, that is accessible via absorption of electromagnetic radiation, and that has a lifetime greater than $10^{-13}$ seconds;

"exposure system" means an optical system plus a light source;

"master" means an originally-fabricated article that can be used to manufacture a tool for replication;

"multiphoton absorption" means simultaneous absorption of two or more photons to reach a reactive, electronic excited state that is energetically inaccessible by the absorption of a single photon of the same energy;

"numerical aperture" means the ratio of the diameter of a lens to its focal length (or 1/f number);

"optical system" means a system for controlling light, the system including at least one element chosen from refractive optical elements such as lenses, reflective optical elements such as mirrors, and diffractive optical elements such as gratings. Optical elements shall also include diffusers, waveguides, and other elements known in the optical arts;

"photochemically effective amounts" (of the components of the photoinitiator system) means amounts sufficient to enable the reactive species to undergo at least partial reaction under the selected exposure conditions (as evidenced, for example, by a change in density, viscosity, color, pH, refractive index, or other physical or chemical property);

"photosensitizer" means a molecule that lowers the energy required to activate a photoinitiator by absorbing light of lower energy than is required by the photoinitiator for activation and interacting with the photoinitiator to produce a photoinitiating species therefrom;

"simultaneous" means two events that occur within the period of $10^{-14}$ seconds or less;

"sufficient light" means light of sufficient intensity and appropriate wavelength to effect multiphoton absorption; and "three-dimensional light pattern" means an optical image wherein the light energy distribution resides in a volume or in multiple planes and not in a single plane.

Reactive Species

Reactive species suitable for use in the photoreactive compositions include both curable and non-curable species. Curable species are generally preferred and include, for example, addition-polymerizable monomers and oligomers and addition-crosslinkable polymers (such as free-radically polymerizable or crosslinkable ethylenically-unsaturated species including, for example, acrylates, methacrylates, and certain vinyl compounds such as styrenes), as well as cationically-polymerizable monomers and oligomers and cationically-crosslinkable polymers (which species are most commonly acid-initiated and which include, for example, epoxies, vinyl ethers, cyanate esters, etc.), and the like, and mixtures thereof.

Suitable ethylenically-unsaturated species are described, for example, by Palazzotto et al. in U.S. Pat. No. 5,545,676 at column 1, line 65, through column 2, line 26, and include mono-, di-, and poly-acrylates and methacrylates (for example, methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight about 200-500, copolymerizable mixtures of acrylated monomers such as those of U.S. Pat. No. 4,652,274, and acrylated oligomers such as those of U.S. Pat. No. 4,642,126); unsaturated amides (for example, methylene bis-acrylamide, methylene bis-methacrylamide, 1,6-hexamethylene bis-acrylamide, diethylene triamine tris-acrylamide and beta-methacrylaminoethyl methacrylate); vinyl compounds (for example, styrene, diallyl phthalate, divinyl succinate, divinyl adipate, and divinyl phthalate); and the like; and mixtures thereof. Suitable reactive polymers include polymers with pendant (meth)acrylate groups, for example, having from 1 to about 50 (meth)acrylate groups per polymer chain. Examples of such polymers include aromatic acid (meth)acrylate half ester resins such as Sarbox™ resins available from Sartomer (for example, Sarbox™ 400, 401, 402, 404, and 405). Other useful reactive polymers curable by free radical chemistry include those polymers that have a hydrocarbyl backbone and pendant peptide groups with free-radically polymerizable functionality attached thereto, such as those described in U.S. Pat. No. 5,235,015 (Ali et al.). Mixtures of two or more monomers, oligomers, and/or reactive polymers can be used if desired. Preferred ethylenically-unsaturated species include acrylates, aromatic acid (meth)acrylate half ester resins, and polymers that have a hydrocarbyl backbone and pendant peptide groups with free-radically polymerizable functionality attached thereto.

Suitable cationically-reactive species are described, for example, by Oxman et al. in U.S. Pat. Nos. 5,998,495 and 6,025,406 and include epoxy resins. Such materials, broadly called epoxides, include monomeric epoxy compounds and epoxides of the polymeric type and can be aliphatic, alicyclic, aromatic, or heterocyclic. These materials generally have, on the average, at least 1 polymerizable epoxy group per molecule (preferably, at least about 1.5 and, more preferably, at least about 2). The polymeric epoxides include linear polymers having terminal epoxy groups (for example, a diglycidyl ether of a polyoxyalkylene glycol), polymers having skeletal oxirane units (for example, polybutadiene polyepoxide), and polymers having pendant epoxy groups (for example, a glycidyl methacrylate polymer or copolymer). The epoxides can be pure compounds or can be mixtures of compounds containing one, two, or more epoxy groups per molecule. These epoxy-containing materials can vary greatly in the nature of their backbone and substituent groups. For example, the backbone can be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups, and the like. The molecular weight of the epoxy-containing materials can vary from about 58 to about 100,000 or more.

Other epoxy-containing materials that are useful include glycidyl ether monomers of the formula

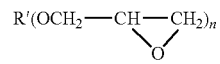

where R' is alkyl or aryl and n is an integer of 1 to 8. Examples are glycidyl ethers of polyhydric phenols obtained by reacting a polyhydric phenol with an excess of a chlorohydrin such as epichlorohydrin (for example, the diglycidyl ether of 2,2- bis-(2,3-epoxypropoxyphenol)-propane). Additional examples of epoxides of this type are described in U.S. Pat. No. 3,018,262, and in *Handbook of Epoxy Resins*, Lee and Neville, McGraw-Hill Book Co., New York (1967).

A number of commercially available epoxy monomers or resins can be used. Epoxides that are readily available include, but are not limited to, octadecylene oxide; epichlorohydrin; styrene oxide; vinylcyclohexene oxide; glycidol; glycidyl methacrylate; diglycidyl ethers of bisphenol A (for example, those available as "EPON 815C", "EPON 813", "EPON 828", "EPON 1004F", and "EPON 1001F" from Hexion Specialty Chemicals, Inc., Columbus, Ohio); and diglycidyl ether of bisphenol F (for example, those available as "ARALDITE GY281" from Ciba Specialty Chemicals Holding Company, Basel, Switzerland, and "EPON 862" from Hexion Specialty Chemicals, Inc.). Other aromatic epoxy resins include the SU-8 resins available from MicroChem. Corp., Newton, Mass.

Other exemplary epoxy monomers include vinyl cyclohexene dioxide (available from SPI Supplies, West Chester, Pa.); 4-vinyl-1-cyclohexene diepoxide (available from Aldrich Chemical Co., Milwaukee, Wis.); 3,4-epoxycyclohexylmethyl-3,4-epoxycyclohexene carboxylate (for example, one available as "CYRACURE UVR-6110" from Dow Chemical Co., Midland, Mich.); 3,4-epoxy-6-methylcyclohexylmethyl-3,4-epoxy-6-methyl-cyclohexane carboxylate; 2-(3,4-epoxycyclohexyl-5,5-spiro-3,4-epoxy)cyclohexane-metadioxane; bis(3,4-epoxycyclohexylmethyl) adipate (for example, one available as "CYRACURE UVR-6128" from Dow Chemical Co.); bis(3,4-epoxy-6-methylcyclohexylmethyl)adipate; 3,4-epoxy-6-methylcyclohexane carboxylate; and dipentene dioxide.

Still other exemplary epoxy resins include epoxidized polybutadiene (for example, one available as "POLY BD 605E" from Sartomer Co., Inc., Exton, Pa.); epoxy silanes (for example, 3,4-epoxycyclohexylethyltrimethoxysilane and 3-glycidoxypropyltrimethoxysilane, commercially available from Aldrich Chemical Co., Milwaukee, Wis.); flame retardant epoxy monomers (for example, one available as "DER-542", a brominated bisphenol type epoxy monomer available from Dow Chemical Co., Midland, Mich.); 1,4-butanediol diglycidyl ether (for example, one available as "ARALDITE RD-2" from Ciba Specialty Chemicals); hydrogenated bisphenol A-epichlorohydrin based epoxy monomers (for example, one available as "EPONEX 1510" from Hexion Specialty Chemicals, Inc.); polyglycidyl ether of phenol-formaldehyde novolak (for example, one available as "DEN-431" and "DEN-438" from Dow Chemical Co.); and epoxidized vegetable oils such as epoxidized linseed and soybean oils available as "VIKOLOX" and "VIKOFLEX" from Atofina Chemicals (Philadelphia, Pa.).

Additional suitable epoxy resins include alkyl glycidyl ethers commercially available from Hexion Specialty Chemicals, Inc. (Columbus, Ohio) as "HELOXY". Exemplary monomers include "HELOXY MODFIER 7" (a $C_8$-$C_{10}$ alkyl glycidyl ether), "HELOXY MODIFIER 8" (a $C_{12}$-$C_{14}$ alkyl glycidyl ether), "HELOXY MODIFIER 61" (butyl glycidyl ether), "HELOXY MODIFER 62" (cresyl glycidyl ether), "HELOXY MODIFER 65" (p-tert-butylphenyl glycidyl ether), "HELOXY MODIFER 67" (diglycidyl ether of 1,4-butanediol), "HELOXY 68" (diglycidyl ether of neopentyl glycol), "HELOXY MODIFER 107" (diglycidyl ether of cyclohexanedimethanol), "HELOXY MODIFER 44" (trimethylol ethane triglycidyl ether), "HELOXY MODIFIER 48" (trimethylol propane triglycidyl ether), "HELOXY MODIFER 84" (polyglycidyl ether of an aliphatic polyol), and "HELOXY MODIFER 32" (polyglycol diepoxide).

Other useful epoxy resins comprise copolymers of acrylic acid esters of glycidol (such as glycidyl acrylate and glycidyl methacrylate) with one or more copolymerizable vinyl compounds. Examples of such copolymers are 1:1 styrene-glycidyl methacrylate and 1:1 methyl methacrylate-glycidyl acrylate. Other useful epoxy resins are well known and contain such epoxides as epichlorohydrins, alkylene oxides (for example, propylene oxide), styrene oxide, alkenyl oxides (for example, butadiene oxide), and glycidyl esters (for example, ethyl glycidate).

Useful epoxy-functional polymers include epoxy-functional silicones such as those described in U.S. Pat. No. 4,279,717 (Eckberg et al.), which are commercially available from the General Electric Company. These are polydimethylsiloxanes in which 1-20 mole % of the silicon atoms have been substituted with epoxyalkyl groups (preferably, epoxy cyclohexylethyl, as described in U.S. Pat. No. 5,753,346 (Leir et al.).

Blends of various epoxy-containing materials can also be utilized. Such blends can comprise two or more weight average molecular weight distributions of epoxy-containing compounds (such as low molecular weight (below 200), intermediate molecular weight (about 200 to 11000), and higher molecular weight (above about 1000)). Alternatively or additionally, the epoxy resin can contain a blend of epoxy-containing materials having different chemical natures (such as aliphatic and aromatic) or functionalities (such as polar and non-polar). Other cationically-reactive polymers (such as vinyl ethers and the like) can additionally be incorporated, if desired.

Preferred epoxies include aromatic glycidyl epoxies (for example, the EPON resins available from Hexion Specialty Chemicals, Inc. and the SU-8 resins available from MicroChem Corp., Newton, Mass.), and the like, and mixtures thereof. More preferred are the SU-8 resins and mixtures thereof.

Suitable cationically-reactive species also include vinyl ether monomers, oligomers, and reactive polymers (for example, methyl vinyl ether, ethyl vinyl ether, tert-butyl vinyl ether, isobutyl vinyl ether, triethyleneglycol divinyl ether (RAPI-CURE DVE-3, available from International Specialty Products, Wayne, N.J.), trimethylolpropane trivinyl ether, and the VECTOMER divinyl ether resins from Morflex, Inc., Greensboro, N.C. (for example, VECTOMER 1312, VECTOMER 4010, VECTOMER 4051, and VECTOMER 4060 and their equivalents available from other manufacturers)), and mixtures thereof. Blends (in any proportion) of one or more vinyl ether resins and/or one or more epoxy resins can also be utilized. Polyhydroxy-functional materials (such as those described, for example, in U.S. Pat. No. 5,856,373 (Kaisaki et al.)) can also be utilized in combination with epoxy- and/or vinyl ether-functional materials.

Non-curable species include, for example, reactive polymers whose solubility can be increased upon acid- or radical-induced reaction. Such reactive polymers include, for example, aqueous insoluble polymers bearing ester groups that can be converted by photogenerated acid to aqueous soluble acid groups (for example, poly(4-tert-butoxycarbonyloxystyrene). Non-curable species also include the chemically-amplified photoresists described by R. D. Allen et al. in "High Performance Acrylic Polymers for Chemically Amplified Photoresist Applications," J. Vac. Sci. Technol. B, 9, 3357 (1991). The chemically-amplified photoresist concept is now widely used for microchip manufacturing, especially with sub-0.5 micron (or even sub-0.2 micron) features. In such photoresist systems, catalytic species (typically hydrogen ions) can be generated by irradiation, which induces a cascade of chemical reactions. This cascade occurs when hydrogen ions initiate reactions that generate more hydrogen ions or other acidic species, thereby amplifying reaction rate. Examples of typical acid-catalyzed chemically-amplified photoresist systems include deprotection (for example, t-butoxycarbonyloxystyrene resists as described in U.S. Pat. No. 4,491,628, tetrahydropyran (THP) methacrylate-based materials, THP-phenolic materials such as those described in U.S. Pat. No. 3,779,778, t-butyl methacrylate-based materials such as those described by R. D Allen et al. in Proc. SPIE 2438, 474 (1995), and the like); depolymerization (for example, polyphthalaldehyde-based materials); and rearrangement (for example, materials based on the pinacol rearrangements).

If desired, mixtures of different types of reactive species can be utilized in the photoreactive compositions. For example, mixtures of free-radically-reactive species and cationically-reactive species are also useful.

Photoinitiator System

The photoinitiator system is a multiphoton photoinitiator system, as the use of such a system enables polymerization to be confined or limited to the focal region of a focused beam of light. Such a system preferably is a two- or three-component system that comprises at least one multiphoton photosensitizer, at least one photoinitiator (or electron acceptor), and, optionally, at least one electron donor. Such multi-component systems can provide enhanced sensitivity, enabling photoreaction to be effected in a shorter period of time and thereby reducing the likelihood of problems due to movement of the sample and/or one or more components of the exposure system.

Preferably, the multiphoton photoinitiator system comprises photochemically effective amounts of (a) at least one multiphoton photosensitizer that is capable of simultaneously absorbing at least two photons and that, optionally but preferably, has a two-photon absorption cross-section greater than that of fluorescein; (b) optionally, at least one electron donor compound different from the multiphoton photosensitizer and capable of donating an electron to an electronic excited state of the photosensitizer; and (c) at least one photoinitiator that is capable of being photosensitized by accepting an electron from an electronic excited state of the photosensitizer, resulting in the formation of at least one free radical and/or acid.

Alternatively, the multiphoton photoinitiator system can be a one-component system that comprises at least one photoinitiator. Photoinitiators useful as one-component multi-photon photoinitiator systems include acyl phosphine oxides (for example, those sold by Ciba under the trade name Irgacure 819, as well as 2,4,6 trimethyl benzoyl ethoxyphenyl phosphine oxide sold by BASF Corporation under the trade name Lucirin™ TPO-L) and stilbene derivatives with covalently attached sulfonium salt moieties (for example, those described by W. Zhou et al. in Science 296, 1106 (2002)). Other conventional ultraviolet (UV) photoinitiators such as benzil ketal can also be utilized, although their multi-photon photoinitiation sensitivities will generally be relatively low.

Multiphoton photosensitizers, electron donors, and photoinitiators (or electron acceptors) useful in two- and three-component multiphoton photoinitiator systems are described below.

(1) Multiphoton Photosensitizers

Multiphoton photosensitizers suitable for use in the multiphoton photoinitiator system of the photoreactive compositions are those that are capable of simultaneously absorbing at least two photons when exposed to sufficient light. Preferably, the photosensitizers have a two-photon absorption cross-section greater than that of fluorescein (that is, greater than that of 3',6'-dihydroxyspiro[isobenzofuran-1(3H), 9'-[9H]xanthen]3-one). Generally, the preferred cross-section can be greater than about $50 \times 10^{-50}$ $cm^4$ sec/photon, as measured by the method described by C. Xu and W. W. Webb in J. Opt. Soc. Am. B, 13, 481 (1996) (which is referenced by Marder and Perry et al. in International Publication No. WO 98/21521 at page 85, lines 18-22).

More preferably, the two-photon absorption cross-section of the photosensitizer is greater than about 1.5 times that of fluorescein (or greater than about $75 \times 10^{-50}$ $cm^4$ sec/photon, as measured by the above method); even more preferably, greater than about twice that of fluorescein (or greater than about $100 \times 10^{-50}$ $cm^4$ sec/photon); most preferably, greater than about three times that of fluorescein (or, alternatively, greater than about $150 \times 10^{-50}$ $cm^4$ sec/photon); and optimally, greater than about four times that of fluorescein (or, alternatively, greater than about $200 \times 10^{-50}$ $cm^4$ sec/photon).

Preferably, the photosensitizer is soluble in the reactive species (if the reactive species is liquid) or is compatible with the reactive species and with any binders (as described below) that are included in the composition. Most preferably, the photosensitizer is also capable of sensitizing 2-methyl-4,6-bis(trichloromethyl)-s-triazine under continuous irradiation in a wavelength range that overlaps the single photon absorption spectrum of the photosensitizer (single photon absorption conditions), using the test procedure described in U.S. Pat. No. 3,729,313.

Preferably, a photosensitizer can also be selected based in part upon shelf stability considerations. Accordingly, selection of a particular photosensitizer can depend to some extent upon the particular reactive species utilized (as well as upon the choices of electron donor compound and/or photoinitiator).

Particularly preferred multiphoton photosensitizers include those exhibiting large multiphoton absorption cross-sections, such as Rhodamine B (that is, N-[9-(2-carboxyphenyl)-6-(diethylamino)-3H-xanthen-3-ylidene]-N-ethylethanaminium chloride or hexafluoroantimonate) and the four classes of photosensitizers described, for example, by Marder and Perry et al. in International Patent Publication Nos. WO 98/21521 and WO 99/53242. The four classes can be described as follows: (a) molecules in which two donors are connected to a conjugated π (pi)-electron bridge; (b) molecules in which two donors are connected to a conjugated π (pi)-electron bridge which is substituted with one or more electron accepting groups; (c) molecules in which two acceptors are connected to a conjugated π (pi)-electron bridge; and (d) molecules in which two acceptors are connected to a conjugated π (pi)-electron bridge which is substituted with one or more electron donating groups (where "bridge" means a molecular fragment that connects two or more chemical groups, "donor" means an atom or group of atoms with a low ionization potential that can be bonded to a conjugated π (pi)-electron bridge, and "acceptor" means an atom or group of atoms with a high electron affinity that can be bonded to a conjugated π (pi)-electron bridge).

The four above-described classes of photosensitizers can be prepared by reacting aldehydes with ylides under standard Wittig conditions or by using the McMurray reaction, as detailed in International Patent Publication No. WO 98/21521.

Other compounds are described by Reinhardt et al. (for example, in U.S. Pat. Nos. 6,100,405, 5,859,251, and 5,770,737) as having large multiphoton absorption cross-sections, although these cross-sections were determined by a method other than that described above.

Preferred photosensitizers include the following compounds (and mixtures thereof):
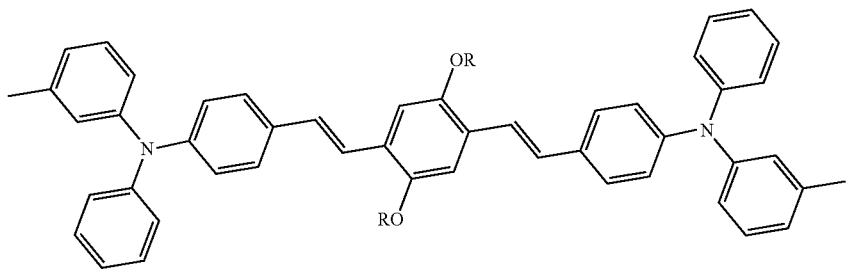
R = C$_{12}$H$_{25}$
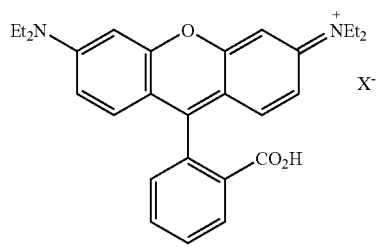
where X$^-$ = Cl$^-$, PF$_6^-$, SbF$_6^-$, AsF$_6^-$, BF$_4^-$, CF$_3$SO$_3^-$
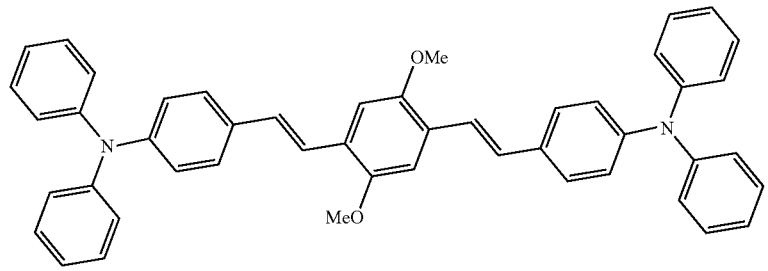
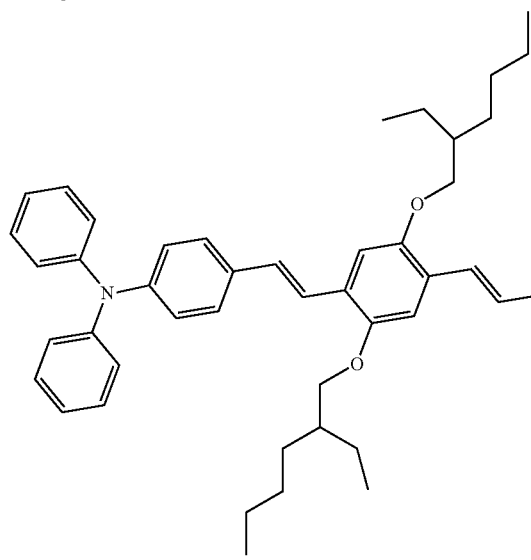
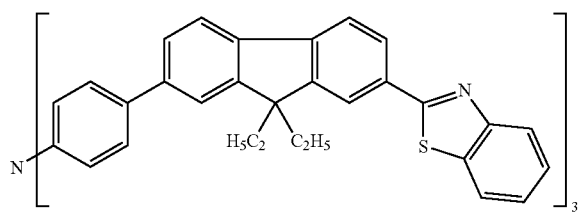

(2) Electron Donor Compounds

Electron donor compounds useful in the multiphoton photoinitiator system of the photoreactive compositions are those compounds (other than the photosensitizer itself) that are capable of donating an electron to an electronic excited state of the photosensitizer. Such compounds may be used, optionally, to increase the multiphoton photosensitivity of the photoinitiator system, thereby reducing the exposure required to effect photoreaction of the photoreactive composition. The electron donor compounds preferably have an oxidation potential that is greater than zero and less than or equal to that of p-dimethoxybenzene. Preferably, the oxidation potential is between about 0.3 and 1 volt vs. a standard saturated calomel electrode ("S.C.E.").

The electron donor compound is also preferably soluble in the reactive species and is selected based in part upon shelf stability considerations (as described above). Suitable donors are generally capable of increasing the speed of cure or the image density of a photoreactive composition upon exposure to light of the desired wavelength.

When working with cationically-reactive species, those skilled in the art will recognize that the electron donor compound, if of significant basicity, can adversely affect the cationic reaction. (See, for example, the discussion in U.S. Pat. No. 6,025,406 (Oxman et al.) at column 7, line 62, through column 8, line 49.)

In general, electron donor compounds suitable for use with particular photosensitizers and photoinitiators can be selected by comparing the oxidation and reduction potentials of the three components (as described, for example, in U.S. Pat. No. 4,859,572 (Farid et al.)). Such potentials can be measured experimentally (for example, by the methods described by R. J. Cox, *Photographic Sensitivity*, Chapter 15, Academic Press (1973)) or can be obtained from references such as N. L. Weinburg, Ed., *Technique of Electroorganic Synthesis Part II Techniques of Chemistry*, Vol. V (1975), and C. K. Mann and K. K. Barnes, *Electrochemical Reactions in Nonaqueous Systems* (1970). The potentials reflect relative energy relationships and can be used to guide electron donor compound selection.

Suitable electron donor compounds include, for example, those described by D. F. Eaton in *Advances in Photochemistry*, edited by B. Voman et al., Volume 13, pp. 427-488, John Wiley and Sons, New York (1986); by Oxman et al. in U.S. Pat. No. 6,025,406 at column 7, lines 42-61; and by Palazzotto et al. in U.S. Pat. No. 5,545,676 at column 4, line 14 through column 5, line 18. Such electron donor compounds include amines (including triethanolamine, hydrazine, 1,4-diazabicyclo[2.2.2]octane, triphenylamine (and its triphenylphosphine and triphenylarsine analogs), aminoaldehydes, and aminosilanes), amides (including phosphoramides), ethers (including thioethers), ureas (including thioureas), sulfinic acids and their salts, salts of ferrocyanide, ascorbic acid and its salts, dithiocarbamic acid and its salts, salts of xanthates, salts of ethylene diamine tetraacetic acid, salts of $(alkyl)_n(aryl)_m$ borates (n+m=4) (tetraalkylammonium salts preferred), various organometallic compounds such as $SnR_4$ compounds (where each R is independently chosen from among alkyl, aralkyl (particularly, benzyl), aryl, and alkaryl groups) (for example, such compounds as $n-C_3H_7Sn(CH_3)_3$, $(allyl)Sn(CH_3)_3$, and $(benzyl)Sn(n-C_3H_7)_3$), ferrocene, and the like, and mixtures thereof. The electron donor compound can be unsubstituted or can be substituted with one or more non-interfering substituents. Particularly preferred electron donor compounds contain an electron donor atom (such as a nitrogen, oxygen, phosphorus, or sulfur atom) and an abstractable hydrogen atom bonded to a carbon or silicon atom alpha to the electron donor atom.

Preferred amine electron donor compounds include alkyl-, aryl-, alkaryl- and aralkyl-amines (for example, methylamine, ethylamine, propylamine, butylamine, triethanolamine, amylamine, hexylamine, 2,4-dimethylaniline, 2,3-dimethylaniline, o-, m- and p-toluidine, benzylamine, aminopyridine, N,N'-dimethylethylenediamine, N,N'-diethylethylenediamine, N,N'-dibenzylethylenediamine, N,N'-diethyl-1,3-propanediamine, N,N'-diethyl-2-butene-1,4-diamine, N,N'-dimethyl-1,6-hexanediamine, piperazine, 4,4'-trimethylenedipiperidine, 4,4'-ethylenedipiperidine, p-N,N-dimethyl-aminophenethanol and p-N-dimethylaminobenzonitrile); aminoaldehydes (for example, p-N,N-dimethylaminobenzaldehyde, p-N,N-diethylaminobenzaldehyde, 9-julolidine carboxaldehyde, and 4-morpholinobenzaldehyde); and aminosilanes (for example, trimethylsilylmorpholine, trimethylsilylpiperidine, bis(dimethylamino)diphenylsilane, tris(dimethylamino)methylsilane, N,N-diethylaminotrimethylsilane, tris(dimethylamino)phenylsilane, tris(methylsilyl)amine, tris(dimethylsilyl)amine, bis(dimethylsilyl)amine, N,N-bis(dimethylsilyl)aniline, N-phenyl-N-dimethylsilylaniline, and N,N-dimethyl-N-dimethylsilylamine); and mixtures thereof. Tertiary aromatic alkylamines, particularly those having at least one electron-withdrawing group on the aromatic ring, have been found to provide especially good shelf stability. Good shelf stability has also been obtained using amines that are solids at room temperature. Good photosensitivity has been obtained using amines that contain one or more julolidinyl moieties.

Preferred amide electron donor compounds include N,N-dimethylacetamide, N,N-diethylacetamide, N-methyl-N-phenylacetamide, hexamethylphosphoramide, hexaethylphosphoramide, hexapropylphosphoramide, trimorpholinophosphine oxide, tripiperidinophosphine oxide, and mixtures thereof.

Preferred alkylarylborate salts include
$Ar_3B^-(n-C_4H_9)N^+(C_2H_5)_4$
$Ar_3B^-(n-C_4H_9)N^+(CH_3)_4$
$Ar_3B^-(n-C_4H_9)N^+(n-C_4H_9)_4$
$Ar_3B^-(n-C_4H_9)Li^+$
$Ar_3B^-(n-C_4H_9)N^+(C_6H_{13})_4$
$Ar_3B^-$—$(C_4H_9)N^+(CH_3)_3(CH_2)_2CO_2(CH_2)_2CH_3$
$Ar_3B^-$—$(C_4H_9)N^+(CH_3)_3(CH_2)_2OCO(CH_2)_2CH_3$
$Ar_3B^-$-$(sec-C_4H_9)N^+(CH_3)_3(CH_2)_2CO_2(CH_2)_2CH_3$
$Ar_3B^-$-$(sec-C_4H_9)N^+(C_6H_{13})_4$
$Ar_3B^-$—$(C_4H_9)N^+(C_8H_{17})_4$
$Ar_3B^-$—$(C_4H_9)N^+(CH_3)_4$
$(p-CH_3O$—$C_6H_4)_3B^-(n-C_4H_9)N^+(n-C_4H_9)_4$
$Ar_3B^-$—$(C_4H_9)N^+(CH_3)_3(CH_2)_2OH$
$ArB^-(n-C_4H_9)_3N^+(CH_3)_4$
$ArB^-(C_2H_5)_3N^+(CH_3)_4$
$Ar_2B^-(n-C_4H_9)_2N^+(CH_3)_4$
$Ar_3B^-(C_4H_9)N^+(C_4H_9)_4$
$Ar_4B^-N^+(C_4H_9)_4$
$ArB^-(CH_3)_3N^+(CH_3)_4$
$(n-C_4H_9)_4B^-N^+(CH_3)_4$
$Ar_3B^-(C_4H_9)P^+(C_4H_9)_4$
(where Ar is phenyl, naphthyl, substituted (preferably, fluoro-substituted) phenyl, substituted naphthyl, and like groups having greater numbers of fused aromatic rings), as well as tetramethylammonium n-butyltriphenylborate and tetrabutylammonium n-hexyl-tris(3-fluorophenyl)borate, and mixtures thereof.

Suitable ether electron donor compounds include 4,4'-dimethoxybiphenyl, 1,2,4-trimethoxybenzene, 1,2,4,5-tetramethoxybenzene, and the like, and mixtures thereof. Suitable urea electron donor compounds include N,N'-dimethylurea, N,N-dimethylurea, N,N'-diphenylurea, tetramethylthiourea, tetraethylthiourea, tetra-n-butylthiourea, N,N-di-n-butylthiourea, N,N'-di-n-butylthiourea, N,N-diphenylthiourea, N,N'-diphenyl-N,N'-diethylthiourea, and the like, and mixtures thereof.

Preferred electron donor compounds for free radical-induced reactions include amines that contain one or more julolidinyl moieties, alkylarylborate salts, and salts of aromatic sulfinic acids. However, for such reactions, the electron donor compound can also be omitted, if desired (for example, to improve the shelf stability of the photoreactive composition or to modify resolution, contrast, and reciprocity). Preferred electron donor compounds for acid-induced reactions include 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile, 4-dimethylaminophenethyl alcohol, and 1,2,4-trimethoxybenzene.

(3) Photoinitiators

Suitable photoinitiators (that is, electron acceptor compounds) for the reactive species of the photoreactive compositions are those that are capable of being photosensitized by accepting an electron from an electronic excited state of the multiphoton photosensitizer, resulting in the formation of at least one free radical and/or acid. Such photoinitiators include iodonium salts (for example, diaryliodonium salts), sulfonium salts (for example, triarylsulfonium salts optionally substituted with alkyl or alkoxy groups, and optionally having 2,2' oxy groups bridging adjacent aryl moieties), and the like, and mixtures thereof.

The photoinitiator is preferably soluble in the reactive species and is preferably shelf-stable (that is, does not spontaneously promote reaction of the reactive species when dissolved therein in the presence of the photosensitizer and the electron donor compound). Accordingly, selection of a particular photoinitiator can depend to some extent upon the particular reactive species, photosensitizer, and electron donor compound chosen, as described above. If the reactive species is capable of undergoing an acid-initiated chemical reaction, then the photoinitiator is an onium salt (for example, an iodonium or sulfonium salt).

Suitable iodonium salts include those described by Palazzotto et al. in U.S. Pat. No. 5,545,676 at column 2, lines 28 through 46. Suitable iodonium salts are also described in U.S. Pat. Nos. 3,729,313, 3,741,769, 3,808,006, 4,250,053 and 4,394,403. The iodonium salt can be a simple salt (for example, containing an anion such as Cl$^-$, Br$^-$, I$^-$ or $C_4H_5SO_3^-$) or a metal complex salt (for example, containing $SbF_6^-$, $PF_6^-$, $BF_4^-$, tetrakis(perfluorophenyl)borate, $SbF_5OH^-$ or $AsF_6^-$). Mixtures of iodonium salts can be used if desired.

Examples of useful aromatic iodonium complex salt photoinitiators include diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate; and the like; and mixtures thereof. Aromatic iodonium complex salts can be prepared by metathesis of corresponding aromatic iodonium simple salts (such as, for example, diphenyliodonium bisulfate) in accordance with the teachings of Beringer et al., J. Am. Chem. Soc. 81, 342 (1959).

Preferred iodonium salts include diphenyliodonium salts (such as diphenyliodonium chloride, diphenyliodonium hexafluorophosphate, and diphenyliodonium tetrafluoroborate), diaryliodonium hexafluoroantimonate (for example, SarCat™ SR 1012 available from Sartomer Company), and mixtures thereof.

Useful sulfonium salts include those described in U.S. Pat. No. 4,250,053 (Smith) at column 1, line 66, through column 4, line 2, which can be represented by the formulas:

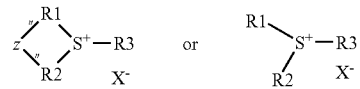

wherein $R_1$, $R_2$, and $R_3$ are each independently selected from aromatic groups having from about 4 to about 20 carbon atoms (for example, substituted or unsubstituted phenyl, naphthyl, thienyl, and furanyl, where substitution can be with such groups as alkoxy, alkylthio, arylthio, halogen, and so forth) and alkyl groups having from 1 to about 20 carbon atoms. As used here, the term "alkyl" includes substituted alkyl (for example, substituted with such groups as halogen, hydroxy, alkoxy, or aryl). At least one of $R_1$, $R_2$, and $R_3$ is aromatic, and, preferably, each is independently aromatic. Z is selected from the group consisting of a covalent bond, oxygen, sulfur, —S(=O)—, —C(=O)—, —(O=)S(=O)—, and —N(R)—, where R is aryl (of about 6 to about 20 carbons, such as phenyl), acyl (of about 2 to about 20 carbons, such as acetyl, benzoyl, and so forth), a carbon-to-carbon bond, or —($R_4$—)C(—$R_5$)—, where $R_4$ and $R_5$ are independently selected from the group consisting of hydrogen, alkyl groups having from 1 to about 4 carbon atoms, and alkenyl groups having from about 2 to about 4 carbon atoms. X$^-$ is an anion, as described below.

Suitable anions, X$^-$, for the sulfonium salts (and for any of the other types of photoinitiators) include a variety of anion types such as, for example, imide, methide, boron-centered, phosphorous-centered, antimony-centered, arsenic-centered, and aluminum-centered anions.

Illustrative, but not limiting, examples of suitable imide and methide anions include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(C_4F_9SO_2)_3C^-$, $(CF_3SO_2)_2(C_4F_9SO_2)C^-$, $(CF_3SO_2)(C_4F_9SO_2)N^-$, $((CF_3)_2NC_2F_4SO_2)_2N^-$, $(CF_3)_2NC_2F_4SO_2C^-(SO_2CF_3)_2$, $(3,5\text{-bis}(CF_3)C_6H_3)SO_2N^-SO_2CF_3$, $C_6H_5SO_2C^-(SO_2CF_3)_2$, $C_6H_5SO_2N^-SO_2CF_3$, and the like. Preferred anions of this type include those represented by the formula $(R_fSO_2)_3C^-$, wherein $R_f$ is a perfluoroalkyl radical having from 1 to about 4 carbon atoms.

Illustrative, but not limiting, examples of suitable boron-centered anions include $F_4B^-$, $(3,5\text{-bis}(CF_3)C_6H_3)_4B^-$, $(C_6F_5)_4B^-$, $(p\text{-}CF_3C_6H_4)_4B^-$, $(m\text{-}CF_3C_6H_4)_4B^-$, $(p\text{-}FC_6H_4)_4B^-$, $(C_6F_5)_3(CH_3)B^-$, $(C_6F_5)_3(n\text{-}C_4H_9)B^-$, $(p\text{-}CH_3C_6H_4)_3(C_6F_5)B^-$, $(C_6F_5)_3FB^-$, $(C_6H_5)_3(C_6F_5)B^-$, $(CH_3)_2(p\text{-}CF_3C_6H_4)_2B^-$, $(C_6F_5)_3(n\text{-}C_{18}H_{37}O)B^-$, and the like. Preferred boron-centered anions generally contain 3 or more halogen-substituted aromatic hydrocarbon radicals attached to boron, with fluorine being the most preferred halogen. Illustrative, but not limiting, examples of the preferred anions include $(3,5\text{-bis}(CF_3)C_6H_3)_4B^-$, $(C_6F_5)_4B^-$, $(C_6F_5)_3(n\text{-}C_4H_9)B^-$, $(C_6F_5)_3FB^-$, and $(C_6F_5)_3(CH_3)B^-$.

Suitable anions containing other metal or metalloid centers include, for example, $(3,5\text{-bis}(CF_3)C_6H_3)_4Al^-$, $(C_6F_5)_4Al^-$, $(C_6F_5)_2F_4P^-$, $(C_6F_5)F_5P^-$, $F_6P^-$, $(C_6F_5)F_5Sb^-$, $F_6Sb^-$, $(HO)F_5Sb^-$, and $F_6As^-$. The foregoing lists are not intended to be exhaustive, as other useful boron-centered nonnucleophilic salts, as well as other useful anions containing other metals or metalloids, will be readily apparent (from the foregoing general formulas) to those skilled in the art.

Preferably, the anion, $X^-$, is selected from tetrafluoroborate, hexafluorophosphate, hexafluoroarsenate, hexafluoroantimonate, and hydroxypentafluoroantimonate (for example, for use with cationically-reactive species such as epoxy resins).

Examples of suitable sulfonium salt photoinitiators include:
triphenylsulfonium tetrafluoroborate
methyldiphenylsulfonium tetrafluoroborate
dimethylphenylsulfonium hexafluorophosphate
triphenylsulfonium hexafluorophosphate
triphenylsulfonium hexafluoroantimonate
diphenylnaphthylsulfonium hexafluoroarsenate
tritolysulfonium hexafluorophosphate
anisyldiphenylsulfonium hexafluoroantimonate
4-butoxyphenyldiphenylsulfonium tetrafluoroborate
4-chlorophenyldiphenylsulfonium hexafluorophosphate
tri(4-phenoxyphenyl)sulfonium hexafluorophosphate
di(4-ethoxyphenyl)methylsulfonium hexafluoroarsenate
4-acetonylphenyldiphenylsulfonium tetrafluoroborate
4-thiomethoxyphenyldiphenylsulfonium hexafluorophosphate
di(methoxysulfonylphenyl)methylsulfonium hexafluoroantimonate
di(nitrophenyl)phenylsulfonium hexafluoroantimonate
di(carbomethoxyphenyl)methylsulfonium hexafluorophosphate
4-acetamidophenyldiphenylsulfonium tetrafluoroborate
dimethylnaphthylsulfonium hexafluorophosphate
trifluoromethyldiphenylsulfonium tetrafluoroborate
p-(phenylthiophenyl)diphenylsulfonium hexafluoroantimonate
10-methylphenoxathiinium hexafluorophosphate
5-methylthianthrenium hexafluorophosphate
10-phenyl-9,9-dimethylthioxanthenium hexafluorophosphate
10-phenyl-9-oxothioxanthenium tetrafluoroborate
5-methyl-10-oxothianthrenium tetrafluoroborate
5-methyl-10,10-dioxothianthrenium hexafluorophosphate Preferred sulfonium salts include triaryl-substituted salts such as triarylsulfonium hexafluoroantimonate (for example, SarCat™ SR1010 available from Sartomer Company), triarylsulfonium hexafluorophosphate (for example, SarCat™ SR 1011 available from Sartomer Company), and triarylsulfonium hexafluorophosphate (for example, SarCat™ KI85 available from Sartomer Company).

Preferred photoinitiators include iodonium salts (more preferably, aryliodonium salts), sulfonium salts, and mixtures thereof. More preferred are aryliodonium salts and mixtures thereof.

Preparation of Photoreactive Composition

The reactive species, multiphoton photosensitizers, electron donor compounds, and photoinitiators can be prepared by the methods described above or by other methods known in the art, and many are commercially available. These four components can be combined under "safe light" conditions using any order and manner of combination (optionally, with stirring or agitation), although it is sometimes preferable (from a shelf life and thermal stability standpoint) to add the photoinitiator last (and after any heating step that is optionally used to facilitate dissolution of other components). Solvent can be used, if desired, provided that the solvent is chosen so as to not react appreciably with the components of the composition. Suitable solvents include, for example, acetone, dichloromethane, and acetonitrile. The reactive species itself can also sometimes serve as a solvent for the other components.

The three components of the photoinitiator system are present in photochemically effective amounts (as defined above). Generally, the composition can contain at least about 5% (preferably, at least about 10%; more preferably, at least about 20%) up to about 99.79% (preferably, up to about 95%; more preferably, up to about 80%) by weight of one or more reactive species; at least about 0.01% (preferably, at least about 0.1%; more preferably, at least about 0.2%) up to about 10% (preferably, up to about 5%; more preferably, up to about 2%) by weight of one or more photosensitizers; optionally, up to about 10% (preferably, up to about 5%) by weight of one or more electron donor compounds (preferably, at least about 0.1%; more preferably, from about 0.1% to about 5%); and from about 0.1% to about 10% by weight of one or more electron acceptor compounds (preferably, from about 0.1% to about 5%) based upon the total weight of solids (that is, the total weight of components other than solvent).

A wide variety of adjuvants can be included in the photoreactive compositions, depending upon the desired end use. Suitable adjuvants include solvents, diluents, resins, binders, plasticizers, pigments, dyes, inorganic or organic reinforcing or extending fillers (at preferred amounts of about 10% to 90% by weight based on the total weight of the composition), thixotropic agents, indicators, inhibitors, stabilizers, ultraviolet absorbers, and the like. The amounts and types of such adjuvants and their manner of addition to the compositions will be familiar to those skilled in the art.

It is within the scope of this invention to include nonreactive polymeric binders in the compositions in order, for example, to control viscosity and to provide film-forming properties. Such polymeric binders can generally be chosen to be compatible with the reactive species. For example, polymeric binders that are soluble in the same solvent that is used for the reactive species, and that are free of functional groups that can adversely affect the course of reaction of the reactive species, can be utilized. Binders can be of a molecular weight suitable to achieve desired film-forming properties and solution rheology (for example, molecular weights between about 5,000 and 1,000,000 Daltons; preferably between about 10,000 and 500,000 Daltons; more preferably, between about 15,000 and 250,000 Daltons). Suitable polymeric binders include, for example, polystyrene, poly(methyl methacrylate), poly(styrene)-co-(acrylonitrile), cellulose acetate butyrate, and the like.

Prior to exposure, the resulting photoreactive compositions can be coated on a substrate, if desired, by any of a variety of coating methods known to those skilled in the art (including, for example, knife coating and spin coating). The substrate can be chosen from a wide variety of films, sheets, and other surfaces (including silicon wafers and glass plates), depending upon the particular application and the method of exposure to be utilized. In some embodiments, the substrate can be made out of a polymer such as, for example, acrylic or polycarbonate. In other embodiments, the substrate can be made out of a metal such as, for example, aluminum, stainless steel, or copper. Copper may be particularly desirable due to its properties in machining and for electroplating of nickel since it does not react with common electroplating chemistries. In some embodiments, the substrate can be provided with a pre-cured base layer by coating the substrate with a layer of photoactive composition and then curing. Preferred substrates are generally sufficiently flat to enable the preparation of a layer of photoreactive composition having a uniform thickness. For applications where coating is less desirable, the photoreactive compositions can alternatively be exposed in bulk form.

Exposure System and Its Use

In carrying out the process of the invention, a photoreactive composition can be exposed to light under conditions such that multiphoton absorption occurs, thereby causing a region of differential solubility characteristics (for example, lesser or greater solubility in a particular solvent) as compared to the photoreactive composition prior to exposure. Such exposure can be accomplished by any known means capable of achieving sufficient intensity of the light.

One exemplary type of system that can be used is shown in FIG. 1. Referring to FIG. 1, fabrication system 10 includes light source 12, optical system 14 comprising a final optical element 15 (optionally including galvo-mirrors and a telescope to control beam divergence), and moveable stage 16. Stage 16 is moveable in one, two, or, more typically, three dimensions. Substrate 18 mounted on stage 16 has a layer 20 of photoreactive composition 24 thereon. Light beam 26 originating from light source 12 passes through optical system 14 and leaves through final optical element 15 which focuses it to a point P within layer 20, thereby controlling the three-dimensional spatial distribution of light intensity within the composition and causing at least a portion of photoreactive composition 24 in the vicinity of point P to become more, or less, soluble in at least one solvent than it was immediately prior to exposure to light beam 26.

By moving stage 16, or by directing light beam 26 (for example, moving a laser beam using galvo-mirrors and a telescope) in combination with moving one or more elements of optical system 14, the focal point P can be scanned or translated in a three-dimensional pattern that corresponds to a desired shape. The resulting reacted or partially reacted portion of photoreactive composition 24 then creates a three-dimensional structure of the desired shape. For example, in a single pass the surface profile (corresponding to a thickness of about one volume pixel or voxel) of one or more microneedles can be exposed or imaged, which upon development can form the surface of the microneedle array.

The exposure or imaging of the surface profile can be carried out by scanning at least the perimeter of a planar slice of a desired three-dimensional structure and then scanning a plurality of preferably parallel, planar slices to complete the structure. Slice thickness can be controlled to achieve a sufficiently high resolution for the shape of a microneedle. For example, smaller slice thicknesses can be desirable in regions of greater structure taper to aid in achieving high structure fidelity, but larger slice thicknesses can be utilized in regions of less structure taper to aid in maintaining useful fabrication times. In this way, highly detailed features having dimensions less than the slice thickness (preferably, less than about one-half of the slice thickness; more preferably, less than about one-quarter of the slice thickness) can be achieved without sacrificing fabrication speed (throughput or number of microneedle arrays fabricated per unit time).

Light source 12 can be any light source that produces sufficient light intensity to effect multiphoton absorption. Suitable sources include, for example, femtosecond near-infrared titanium sapphire oscillators (for example, those available from Coherent, Santa Clara, Calif., as "MIRA OPTIMA 900-F") pumped by an argon ion laser (for example, those available from Coherent as "INNOVA"). This laser, operating at 76 MHz, has a pulse width of less than 200 femtoseconds, is tunable between 700 and 980 nm, and has average power up to 1.4 Watts. Another useful laser is available from Spectra-Physics, Mountain View, Calif., under the trade designation "MAI TAI", tunable to wavelengths in a range of from 750 to 850 nanometers, and having a repetition frequency of 80 megahertz, and a pulse width of about 100 femtoseconds ($1 \times 10^{-13}$ sec), with an average power level up to 1 Watt.

However, any light source (for example, a laser) that provides sufficient intensity to effect multiphoton absorption at a wavelength appropriate for the multiphoton absorber used in the photoreactive composition can be utilized. Such wavelengths can generally be in the range of about 300 to about 1500 nm; preferably, from about 400 to about 1100 nm; more preferably, from about 600 to about 900 nm; more preferably, from about 750 to about 850 nm, inclusive. Typically, the light fluence (for example, peak intensity of a pulsed laser) is greater than about $10^6$ W/cm$^2$. The upper limit on the light fluence is generally dictated by the ablation threshold of the photoreactive composition. For example, Q-switched Nd:YAG lasers (for example, those available from Spectra-Physics as "QUANTA-RAY PRO"), visible wavelength dye lasers (for example, those available from Spectra-Physics as "SIRAH" pumped by a Q-switched Nd:YAG laser from Spectra-Physics having the trade designation "Quanta-Ray PRO"), and Q-switched diode pumped lasers (for example, those available from Spectra-Physics as "FCBAR") can also be utilized.

Preferred light sources are near infrared pulsed lasers having a pulse length less than about $10^{-8}$ second (more preferably, less than about $10^{-9}$ second; most preferably, less than about $10^{-11}$ second). Other pulse lengths can be used as long as the peak intensity and ablation threshold criteria above are met. Pulsed radiation can, for example, have a pulse frequency of from about one kilohertz up to about 50 megahertz, or even more. Continuous wave lasers can also be used.

Optical system 14 can include, for example, refractive optical elements (for example, lenses or microlens arrays), reflective optical elements (for example, retroreflectors or focusing mirrors), diffractive optical elements (for example, gratings, phase masks, and holograms), polarizing optical elements (for example, linear polarizers and waveplates), dispersive optical elements (for example, prisms and gratings), diffusers, Pockels cells, waveguides, and the like. Such optical elements are useful for focusing, beam delivery, beam/mode shaping, pulse shaping, and pulse timing. Generally, combinations of optical elements can be utilized, and other appropriate combinations will be recognized by those skilled in the art. Final optical element 15 can include, for example, one or more refractive, reflective, and/or diffractive optical elements. In one embodiment, an objective such as, for example, those used in microscopy can be conveniently obtained from commercial sources such as, for example, Carl Zeiss, North America, Thornwood, N.Y., and used as final optical element 15. For example, fabrication system 10 can include a scanning confocal microscope (for example, those available from Bio-Rad Laboratories, Hercules, Calif., as "MRC600") equipped with a 0.75 numerical aperture (NA) objective (such as, for example, those available from Carl Zeiss, North America as "20×FLUAR").

It can often be desirable to use optics with relatively large numerical aperture to provide highly-focused light. However, any combination of optical elements that provides a desired intensity profile (and spatial placement thereof) can be utilized.

Exposure times generally depend upon the type of exposure system used to cause reaction of the reactive species in the photoreactive composition (and its accompanying variables such as numerical aperture, geometry of light intensity spatial distribution, the peak light intensity during the laser pulse (higher intensity and shorter pulse duration roughly correspond to peak light intensity)), as well as upon the nature of the photoreactive composition. Generally, higher peak light intensity in the regions of focus allows shorter exposure times, everything else being equal. Linear imaging or "writing" speeds generally can be about 5 to 100,000 microns/second using a laser pulse duration of about $10^{-3}$ to $10^{-15}$ second (for example, about $10^{-11}$ to $10^{-14}$ second) and about $10^2$ to $10^9$ pulses per second (for example, about $10^3$ to $10^8$ pulses per second).

In order to facilitate solvent development of the exposed photoreactive composition and obtain a fabricated microneedle structure, a threshold dose of light (that is, threshold dose) can be utilized. This threshold dose is typically process specific, and can depend on variables such as, for example, the wavelength, pulse frequency, intensity of the light, the specific photoreactive composition, the specific microneedle structure being fabricated, or the process used for solvent development. Thus, each set of process parameters can typically be characterized by a threshold dose. Higher doses of light than the threshold can be used, and can be beneficial, but higher doses (once above the threshold dose) can typically be used with a slower writing speed and/or higher light intensity.

Increasing the dose of light tends to increase the volume and aspect ratio of voxels generated by the process. Thus, in order to obtain voxels of low aspect ratio, it is generally preferable to use a light dose that is less than about 10 times the threshold dose, preferably less than about 4 times the threshold dose, and more preferably less than about 3 times the threshold dose. In order to obtain voxels of low aspect ratio, the radial intensity profile of light beam 26 is preferably Gaussian.

Through multiphoton absorption, light beam 26 induces a reaction in the photoreactive composition that produces a volume region of material having solubility characteristics different from those of the unexposed photoreactive composition. The resulting pattern of differential solubility can then be realized by a conventional development process, for example, by removing either exposed or unexposed regions.

The exposed photoreactive composition can be developed, for example, by placing the exposed photoreactive composition into solvent to dissolve regions of higher solvent solubility, by rinsing with solvent, by evaporation, by oxygen plasma etching, by other known methods, and by combinations thereof. Solvents that can be used for developing the exposed photoreactive composition include aqueous solvents such as, for example, water (for example, having a pH in a range of from 1 to 12) and miscible blends of water with organic solvents (for example, methanol, ethanol, propanol, acetone, acetonitrile, dimethylformamide, N-methylpyrrolidone, and the like, and mixtures thereof); and organic solvents. Exemplary useful organic solvents include alcohols (for example, methanol, ethanol, and propanol), ketones (for example, acetone, cyclopentanone, and methyl ethyl ketone), aromatics (for example, toluene), halocarbons (for example, methylene chloride and chloroform), nitriles (for example, acetonitrile), esters (for example, ethyl acetate and propylene glycol methyl ether acetate), ethers (for example, diethyl ether and tetrahydrofuran), amides (for example, N-methylpyrrolidone), and the like, and mixtures thereof.

An optional bake after exposure to light under multiphoton absorption conditions, but prior to solvent development, can be useful for some photoreactive compositions such as, for example, epoxy-type reactive species. Typical bake conditions include temperatures in a range of from about 40° C. to about 200° C., for times in a range of from about 0.5 minutes to about 20 minutes.

Optionally, after exposure of only the surface profile of a microneedle array, preferably followed by solvent development, a nonimagewise exposure using actinic radiation can be carried out to effect reaction of the remaining unreacted photoreactive composition. Such a nonimagewise exposure can preferably be carried out by using a one-photon process.

Complex three-dimensional microneedles and microneedle arrays can be prepared in this manner.

Microneedles and Microneedle Arrays

Figure 2:
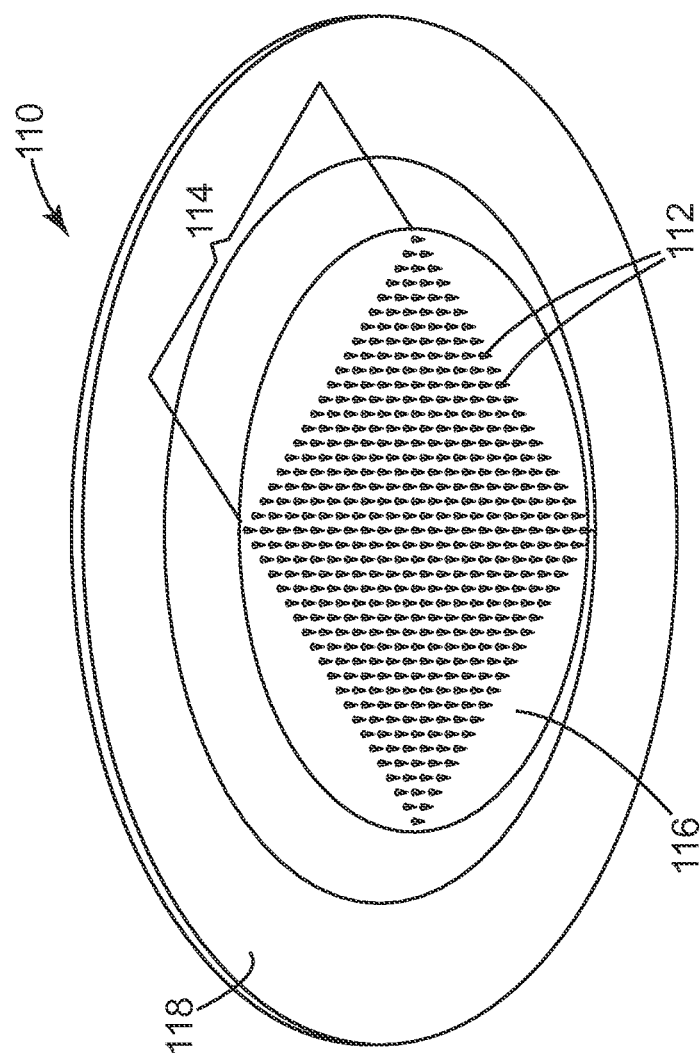
FIG. 2 is a schematic perspective view of a microneedle array.

The process of the invention can be used to prepare microneedle arrays with microneedles integrally formed with a substrate. FIG. 2 shows such a microneedle array 110. A portion of the array 110 is illustrated with microneedles 112 protruding from a microneedle substrate surface 116. The microneedles 112 may be arranged in any desired pattern 114 or distributed over the substrate surface 116 randomly. As shown, in one example, the microneedles 112 are arranged in uniformly spaced rows placed in a rectangular arrangement. In one embodiment, arrays of the present invention have a patient-facing surface area of more than about 0.1 cm² and less than about 20 cm², in some instances, more than about 0.5 cm² and less than about 5 cm². In the embodiment shown in FIG. 2, a portion of the substrate surface 116 is non-patterned. In one embodiment, the non-patterned surface has an area of more than about 1 percent and less than about 75 percent of the total area of the device surface that faces a skin surface of a patient. In one embodiment, the non-patterned surface has an area of more than about 0.10 square inch (0.65 cm²) to less than about 1 square inch (6.5 cm²). In another embodiment (not shown), the microneedles are disposed over substantially the entire surface area of the array 110. The thickness of the substrate surface may vary depending on the desired end use of the microneedle array. In one embodiment, the substrate surface may be less than 200 mil (0.51 cm) in thickness, often less than 100 mil (0.25 cm) in thickness, and sometimes less than 50 mil (0.13 cm) in thickness. The substrate surface is typically more than 1 mil (25.4 µm) in thickness, often more than 5 mil (127 µm) in thickness, and sometimes more than 10 mil (203 µm) in thickness.

The microneedles are typically less than 1000 microns in height, often less than 500 microns in height, and sometimes less than 250 microns in height. The microneedles are typically more than 20 microns in height, often more than 50 microns in height, and sometimes more than 125 microns in height. In one embodiment, the microneedles are between about 50 microns and about 250 microns in height.

The microneedles may be characterized by an aspect ratio. As used herein, the term "aspect ratio" is the ratio of the height of the microneedle (above the surface surrounding the base of the microneedle) to the maximum base dimension, that is, the longest straight-line dimension that the base occupies (on the surface occupied by the base of the microneedle). In the case of a pyramidal microneedle with a rectangular base, the maximum base dimension would be the diagonal line connecting opposed corners across the base. Microneedles of the present invention typically have an aspect ratio of between about 2:1 to about 5:1 and sometimes between about 2.5:1 to about 4:1. In particular, it is often desired that the microneedles are sufficiently tall (e.g., more than 20 microns in height, sometimes more than 50 microns in height) and sufficiently narrow (e.g., having an aspect ratio of 2:1 or more) so as to be able to easily penetrate the stratum corneum. It is also often desired that the microneedles are sufficiently robust (e.g., having an aspect ratio of 5:1 or less, having a suitable tip shape, comprising a tough material, etc.) so that they resist bending or breaking when pressed against the stratum corneum.

Figure 3:
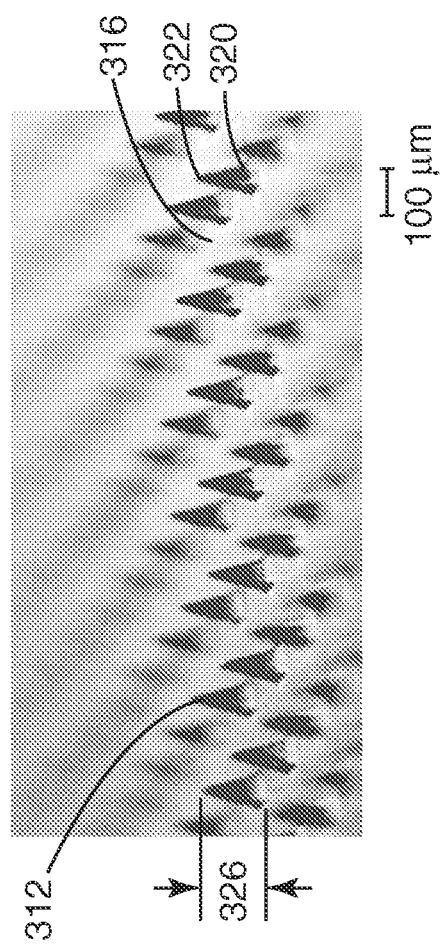
FIG. 3 is a microphotograph of a portion of a microneedle array.

One manner in which the microneedles of the present invention may be characterized is by height 326, as shown in FIG. 3. The height 326 of the microneedles 312 may be measured from the substrate surface 316. It may be preferred, for example, that the base-to-tip height of the microneedles 312 be about 500 micrometers or less as measured from the substrate surface 316. Alternatively, it may be preferred that the height 326 of the microneedles 312 is about 250 micrometers or less as measured from the base 320 to the tip 322. It may also be preferred that the height of molded microneedles is greater than about 90%, and more preferably greater than about 95%, of the height of the microneedle topography in a mold. Microneedles may deform slightly or elongate upon ejection from a mold. This condition is most pronounced if the molded material has not cooled below its softening temperature, but may still occur even after the material is cooled below its softening temperature. It is preferred that the height of molded microneedles is less than about 115%, and more preferably less than about 105%, of the height of the microneedle topography in the mold.

The general shape of the microneedles of the present invention may be tapered. For example, the microneedles 312 may have a larger base 320 at the substrate surface 316 and extend away from the substrate surface 316, tapering to a tip 322. In one embodiment the shape of the microneedles is generally pyramidal. In another embodiment, the shape of the microneedles is generally conical. In one embodiment the microneedles have a defined tip bluntness, such as that described in U.S. Patent Application Publication No. 2005/0261631, the disclosure of which is herein incorporated by reference, wherein the microneedles have a flat tip comprising a surface area measured in a plane aligned with the base of about 20 square micrometers or more and 100 square micrometers or less. In one embodiment, the surface area of the flat tip will be measured as the cross-sectional area measured in a plane aligned with the base, the plane being located at a distance of 0.98 h from the base, where h is the height of the microneedle above the substrate surface measured from base to tip.

Figure 5:
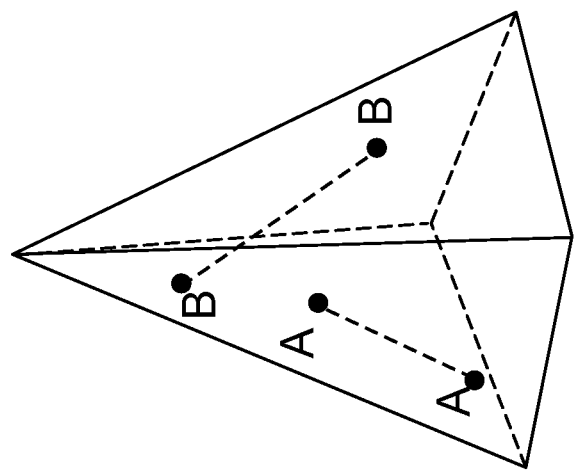
FIG. 5 is a schematic perspective view of another microneedle.
Figure 4:
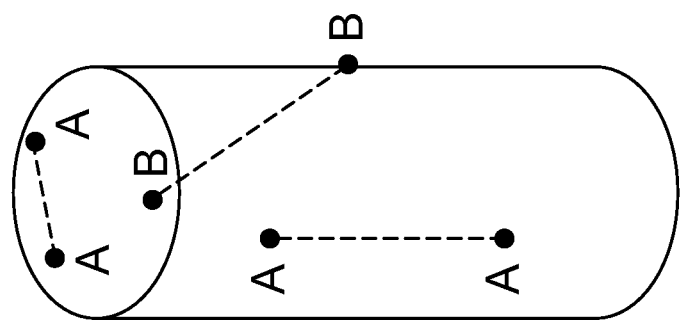
FIG. 4 is a schematic perspective view of a microneedle.

In one embodiment the microneedles are solid, that is, having no holes that pass entirely through the microneedle to form a hollow channel within the needle. In one embodiment, one or more of the microneedles are solid and have an outer surface that is characterized by at least one concave area. A concave area may be defined by an imaginary line connecting two points on the outer surface of a microneedle, where the imaginary line does not pass through or along the outer surface of the microneedle. For example, if a microneedle has the shape of a cylindrical pin, then an imaginary line connecting any two points on the outer surface will either pass through or along the outer surface. This is shown in FIG. 4, where the lines connecting points denoted as "A" lay along the surface of the microneedle and the line connecting the points denoted as "B" passes through the microneedle. Likewise for a regular three- or four-sided pyramid (as shown in FIG. 5 with like labeled points), a regular cone, or an obelisk (i.e., a pyramidal tip on top of a square-sided base). All of the aforementioned shapes lack a concave area in the outer surface of the microneedle. Conversely, shapes such as shown in FIGS. 6 to 10 all have at least one concave area in the outer surface of the microneedle.

FIG. 6 shows a microneedle 150 with a bladed tip having multiple concave areas. As shown, microneedle 150 includes a base 152 affixed to and extending from a supporting substrate (not shown). The shaft 154 extends from the base 152 (and supporting substrate) in a substantially orthogonal manner, forming a second end. Microblade structure 158 is provided on the second end and the microblade structure 158 essentially forms the tip of the microneedle 150. Microblade structure 158 includes four identical wings 160, 162, 164 and 166 with corresponding edges 160a, 162a, 164a and 166a that serve as cutting edges and are capable of slicing through the stratum corneum when the microneedle 150 is pressed against the skin. In the depicted embodiment, the microblade structure 158 is configured so that the first end of each wing 160, 162, 164 and 166 is center point 180. In the depicted configuration, the center-point 180 is also the distal-most point from the substrate supporting the base 152. Consequently, when the microneedle is pressed against the skin, the center point 180 would be first to initiate contact with and subsequently penetrate the stratum corneum while the second end points 190, 192, 194 and 196 of edges 160a, 162a, 164a and 166a would contact the skin after the center point 180. The dotted line connecting edges 166a and 160a illustrates one concave area, as it does not pass along or through the surface of the microneedle. Although shown with four symmetrically-aligned, identical wings, similar structures with a plurality of wings may be prepared, including 2, 3, 5, or more wings. Likewise, the wings need not be identical to each other, nor need they be symmetrically aligned on the base.

Figure 9:
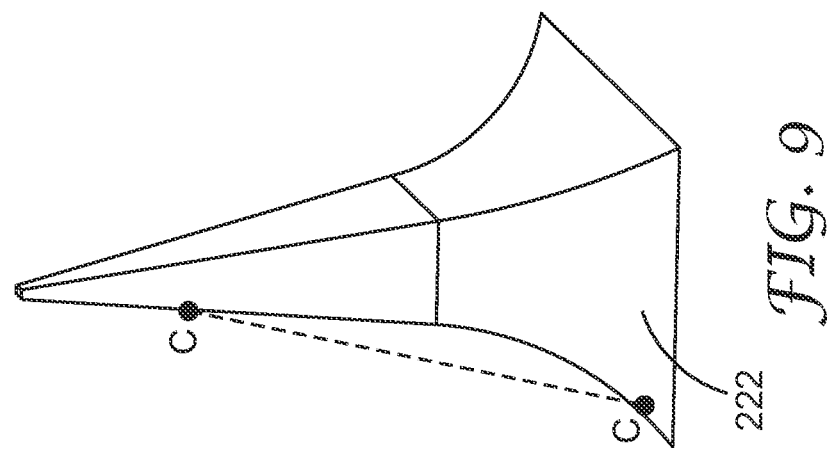
Figure 8:
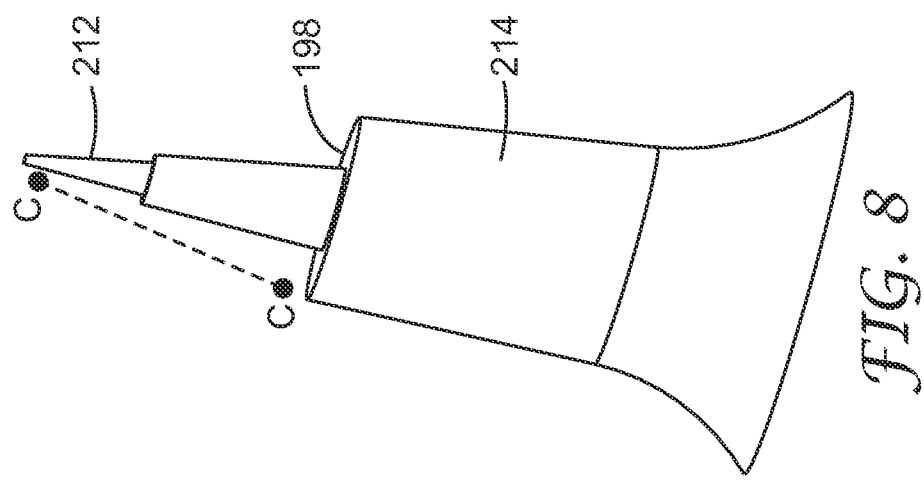

FIG. 7 shows a cross-section of the base of a microneedle having a channel 202 in one side. The line connecting the points denoted as "C" does not pass along or through the surface of the microneedle. FIG. 8 shows a side view of a needle having a smaller tip 212 on a larger base 214, where the line connecting the points denoted as "C" does not pass along or through the surface of the microneedle. FIG. 9 shows a side view of a needle having a flared base 222. In one embodiment, the concave area may be partially defined by a sharp angled inner edge 198 as in FIGS. 6 and 8.

In one embodiment, the base of the microneedles may be flared, that is, the base curves outward from the main axis of the microneedle so as to join an array substrate at a shallower angle than if the base was not flared. Such a shape may, for example, aid in the ability to mold microneedles from a master. In one aspect, the flared base may smoothly or seamlessly meet the substrate without any sharp delineation.

Figure 10:
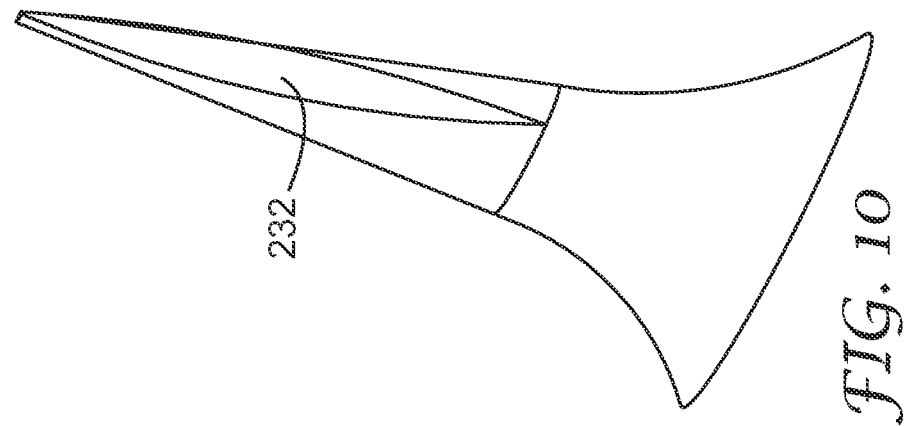
FIGS. 8 to 10 are schematic perspective views of other microneedles.

FIG. 10 shows a side view of a generally conical needle having a flared base and a groove 232 extending from the tip of the microneedle and along part of the outer surface of the microneedle. The groove 232 represents a concave area on the surface of the microneedle. Such a groove need not extend all the way to the tip of the microneedle, and in other embodiments it may extend along the full length of the microneedle. Although not shown, a microneedle may have a plurality of grooves.

In one embodiment, the concave area serves to form a capillary space on the outer surface of the needle which can aid in applying a coating solution to the needle. Additional examples and description of capillary spaces in microneedles may be found in U.S. Patent Application Ser. No. 60/752,418 filed on Dec. 21, 2005, the disclosure of which is herein incorporated by reference.

Figure 16:
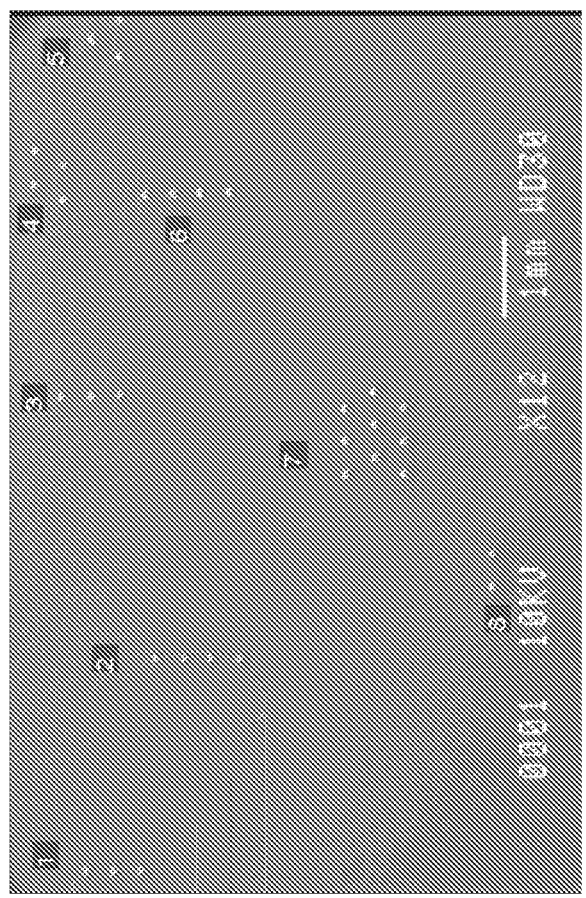
FIG. 16 is a scanning electron micrograph of a microneedle device prepared by a multiphoton polymerization process.

The microneedle arrays prepared by methods of the present invention may comprise any of a variety of configurations, such as those described in the following patents and patent applications, the disclosures of which are herein incorporated by reference. One embodiment for the microneedle devices comprises the structures disclosed in U.S. Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in U.S. Patent Application Publication No. 2005/0261631 which describes microneedles having a truncated tapered shape and a controlled aspect ratio. Still another embodiment for the microneedle arrays comprises the structures disclosed in U.S. Pat. No. 6,312,612 (Sherman, et al.) which describes tapered structures having a hollow central channel. Still another embodiment for the microneedle arrays comprises the structures disclosed in U.S. Pat. No. 6,379,324 (Gartstein, et al.) which describes hollow microneedles having at least one longitudinal blade at the top surface of tip of the microneedle and solid, "star-shaped" microneedles having multiple bladed edges. In some embodiments, the microneedle devices prepared by methods of the invention can contain microneedles having different shapes. For example, the device may have an array of microneedles having a tapered structure that includes at least one channel formed in the outside surface of each microneedle and an array of microneedles having a truncated tapered shape and a controlled aspect ratio. FIG. 16 is a scanning electron micrograph of a portion of a microneedle master containing microneedles with different shapes. It should also be noted that microneedle devices comprising microneedles having at two or more distinct shapes can be made by other known methods used for making microneedles. However, the methods disclosed herein are very useful for such purpose.

Preparation of Replication Tool from Master

A replication tool, such as a mold insert, may be prepared by using a microneedle array prepared as described above as a master. That is, another material is placed against the master to prepare a mold insert having the negative image of the microneedle array. The master is then removed, thus leaving a mold insert which can subsequently be used to prepare additional microneedle arrays. The mold insert will have cavities in the shape of the negative image of a microneedle array. In one embodiment, a metal replication tool is made from a master by electroplating or electroforming a metal, such as nickel, against the master and subsequently removing the master. In another embodiment, a silicone replication tool is made by curing a silicone resin against the master and subsequently removing the master.

In one embodiment, the cavities in the mold insert may be formed from a master having microneedles with a flared base, such as shown in FIGS. 8, 9, and 10. The resulting cavities having such a flared shape may improve the ability to efficiently mold microneedle arrays using the mold insert.

Molding of Polymeric Microneedle Arrays

A replication tool or mold insert, described above, may be used to mold polymeric microneedle arrays. In one embodiment, a mold insert may be placed into an injection molding apparatus, molten polymeric material is injected into the molding apparatus under pressure and allowed to fill the mold insert. After the polymeric material is allowed to cool sufficiently, a molded microneedle array is ejected from the molding apparatus. In one aspect, the mold insert may be heated to an elevated temperature prior to injection of the molten polymeric material to aid in filling of the mold insert and subsequently cooled to aid in ejection of the molded part. Further description regarding temperature cycled injection molding may be found in U.S. Pat. No. 5,376,317 (Maus et al.) and International Publication No. WO 05/82596. In another embodiment, a compressive force may be used to assist during an injection molding process. Further description regarding this so-called injection-compression molding may be found in U.S. Pat. No. 4,489,033 (Uda et al.), U.S. Pat. No. 4,515,543 (Hamner), and U.S. Pat. No. 6,248,281 (Abe et al.), and U.S. Patent Application Ser. No. 60/634,319 filed on Dec. 7, 2004. In addition, ultrasonic energy may be used to assist in filling of the mold insert with molten polymeric material, as described in U.S. Patent Application Ser. No. 60/634,319 filed on Dec. 7, 2004. The disclosures of all of the foregoing molding patents are herein incorporated by reference.

A wide variety of polymeric materials may be suitable for use in molding microneedle arrays. In one embodiment, the material is selected so that it is capable of forming relatively rigid and tough microneedles that resist bending or breaking when applied to a skin surface. In one aspect, the polymeric material has a melt-flow index greater than about 5 g/10 minutes when measured by ASTM D1238 at conditions of 300° C. and 1.2 kg weight. The melt-flow index is often greater than or equal to about 10 g/10 minutes and sometimes greater than or equal to about 20 g/10 minutes. In another embodiment, the tensile elongation at break as measured by ASTM D638 (2.0 in/minute) is greater than about 100 percent. In still another embodiment, the impact strength as measured by ASTM D256, "Notched Izod", (73° F.) is greater than about 5 ft-lb/inches. Examples of suitable materials include polycarbonate, polyetherimide, polyethylene terephthalate, and mixtures thereof. In one embodiment the material is polycarbonate.

EXAMPLES

Objects and advantages of this invention are further illustrated by the following examples, but the particular materials and amounts thereof recited in these examples, as well as other conditions and details, should not be construed to unduly limit this invention. Unless otherwise noted, all procedures were carried out under a dry nitrogen atmosphere with dry and deoxygenated solvents and reagents. Unless otherwise noted, all solvents and reagents were or can be obtained from Aldrich Chemical Co., Milwaukee, Wis.

Rhodamine B hexafluoroantimonate was prepared by metathesis of Rhodamine B chloride with sodium hexafluoroantimonate.

As used herein,

"SR368" refers to tris-(2-hydroxyethyl)isocyanurate triacrylate, obtained from Sartomer Co., Inc., Exton, Pa.;

"SR9008" refers to a trifunctional acrylate ester obtained from Sartomer Co., Inc., Exton, Pa.;

"SR1012" refers to diaryliodonium hexafluoroantimonate, obtained from Sartomer Co., Inc., Exton, Pa.;

"SU-8 R2150" refers to an epoxy negative photoresist obtained from MicroChem. Corp., Newton, Mass.;

"THF" refers to tetrahydrofuran;

"PHOTOMER 6210" refers to an aliphatic urethane diacrylate, manufactured by Cognis Corp. USA, Cincinnati, Ohio;

"SARTOMER 238" refers to hexanediol diacrylate, available from Sartomer Co., Inc., Exton, Pa.;

"IRGACURE 819" refers to an acylphosphine oxide photoinitiator, available from Ciba Specialty Chemicals, Tarrytown, N.Y.;

Example 1

A circular silicon wafer (10.2 cm (4 inches) in diameter; obtained from Wafer World, Inc., West Palm Beach, Fla.) was cleaned by soaking it for approximately ten minutes in a 3:1 volume/volume (v/v) mixture of concentrated sulfuric acid and 30 weight percent aqueous hydrogen peroxide. The wafer was then rinsed with deionized water and then with isopropanol, after which it was dried under a stream of air. The wafer was then dipped into a two weight percent solution of 3-(trimethoxysilyl)propyl methacrylate in 190-proof ethanol that had been made acidic (pH between 4 and 5) with acetic acid. The wafer was then rinsed with absolute ethanol and was then heated in an oven at 130° C. for ten minutes.

Poly(methyl methacrylate), having a number average molecular weight of approximately 120,000, SR9008, and SR368 were combined in a weight ratio of 30:35:35 to provide a monomer mixture, and this monomer mixture was dissolved in sufficient 1,2-dichloroethane to afford a solution that was 54 weight percent of the monomer mixture. To this solution there were then added aliquots of concentrated solutions of photosensitizer Rhodamine B hexafluoroantimonate in THF and SR1012 in THF sufficient to give a coating solution that was 0.5 weight percent Rhodamine B hexafluoroantimonate and 1.0 weight percent SR1012, based on the total weight of solids. This coating solution was filtered through a 1-micron syringe filter and was poured onto the silicon wafer. The wafer was placed in a forced air oven at 60° C. for 18 hours to afford a coated silicon wafer with a substantially solvent-free (hereinafter, "dry") coating thickness of approximately 300 µm.

The wafer was then mounted on a porous carbon vacuum chuck (flatness >1 µm). The two-photon fabrication system was then activated to produce an optical signal that was stationary in the vertical position (the fabrication system was not activating the z-control to move the signal in the vertical direction). The signal was used as a detection mechanism to produce a reflection off of the wafer surface in conjunction with a confocal microscope system such that the only condition that would produce a confocal response would occur when the optical signal was focused on the surface of the wafer. After the surface of the wafer was detected using this system, the wafer was moved under the signal to detect if the wafer was in the optical plane of the fabrication system. Adjustments were made to a 3-point leveling system that held the carbon vacuum chuck until the wafer was contained in the optical plane to less than 500 nm in 4 points that were outside of the planned fabrication area. The wafer was finally repositioned to an area within the detected surface positions, and the fabrication process was started.

Two-photon polymerization of the dry coating was carried out in the following manner, using a diode-pumped Ti:sapphire laser (Spectra-Physics, Mountain View, Calif.) operating at a wavelength of 800 nm, nominal pulse width of 80 fs, pulse repetition rate of 80 MHz, and average power of approximately 1 W. The coated wafer was placed on a computer-controllable three-axis stage (obtained from Aerotech, Inc., Pittsburgh, Pa.). The laser beam was attenuated by neutral density filters and was focused into the dry coating using a galvoscanner with telescope for x, y, and z-axis control (available from Nutfield Technology, Inc., Windham, N.H.) and a lens (Nikon CFI Plan Achromat 50× oil objective N.A. 0.90, working distance 0.400 mm, 4.0 mm focal length.) which was applied directly on the surface of the dry coating. The average power was measured at the output of the objective lens using a wavelength-calibrated photodiode (obtained from Ophir Optronics, Ltd., Wilmington, Mass.) and was determined to be approximately 8 mW. After the fabrication process was completed, the microneedle array was developed using MicroChem SU-8 solvent, leaving behind the polymerized structures.

Figure 12:
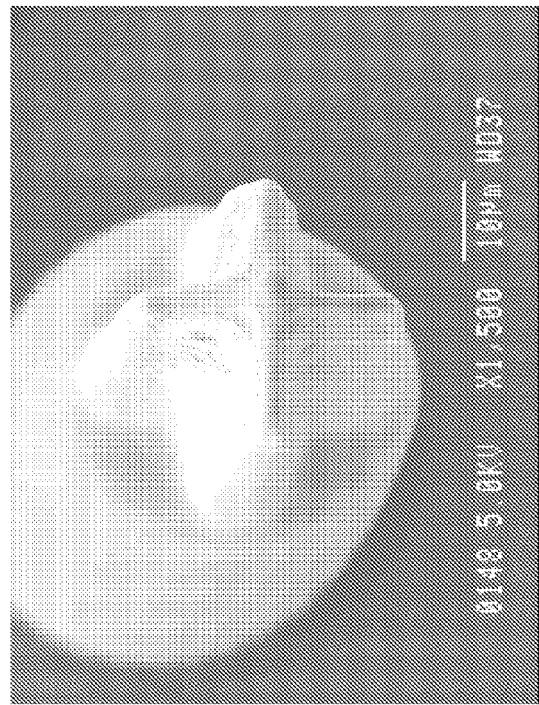
FIG. 12 is a scanning electron micrograph of a single microneedle prepared by a multiphoton polymerization process.
Figure 11:
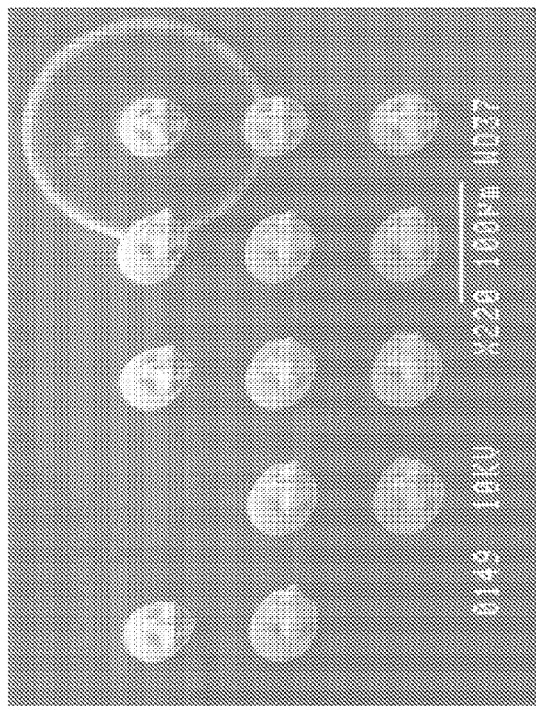
FIG. 11 is a scanning electron micrograph of a microneedle array prepared by a multiphoton polymerization process.

The resultant microneedle array was circular in shape with a 1.2 cm diameter. The needles were arranged in a hexagonal packing arrangement with an average height of 250 µm and a 275 µm tip-to-tip separation between needles. Scanning electron micrographs of portions of the resulting microneedle array are shown in FIGS. 11 and 12.

Example 2

The masterform array of Example 1 was used to create a silicone replication tool (or mold) with an inverse pattern. The procedure for preparing the inverse replication tool used General Electric RTV silicone (part number 615) in a mixture of 10:1 parts A and B, respectively. The solution was stirred by hand for approximately 2 minutes, then stirred mechanically for approximately 30 minutes. The solution was then poured over the two photon-produced array and contained by an aluminum ring about 9/16 inches (1.43 cm) high and an appropriately large diameter to fit beyond the perimeter of the array. The sample was placed in a vacuum chamber at 30 psi ($2.07 \times 10^5$ Pascal) for about 1 hour to minimize entrapment of small air bubbles in the silicone solution. The sample was placed in an oven at 55° C. for approximately 100 minutes to cure the silicone. The sample was allowed to cool, and then removed from the masterform, leaving behind the replication tool having an inverse pattern of the masterform.

The replication tool was used to replicate the two photon pattern using an acrylate material. The procedure included the steps of preparing a 3:1 solution of Photomer 6210 and Sartomer 238 materials with 1.5% (by weight) CGI 819. The Sartomer 238 and CGI 819 were mixed together for 45 minutes and filtered with a 0.2 micron PTFE filter. The Photomer 6210 was warmed to 55° C. for 30 minutes and added to the solution and mixed for 1 hour. The solution was poured onto the silicone mold and then placed in a vacuum oven at 30 psi ($2.07 \times 10^5$ Pascal) for 45 minutes to remove any included air bubbles. Excess solution was allowed to drip off before the mold was placed down on a coated glass slide. Sufficient pressure was added manually to the top of the silicone mold to achieve a desired level of flatness. The sample was then fully cured using an ultraviolet lamp processor (H-type bulb) and allowed to cool before releasing the silicone replication tool from the acrylate part.

Figure 14:
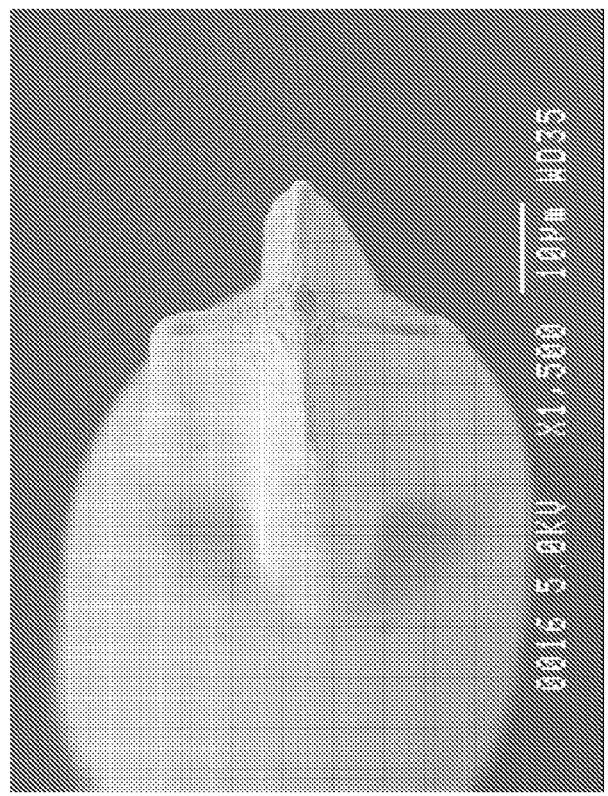
FIG. 14 is a scanning electron micrograph of a molded single microneedle.
Figure 13:
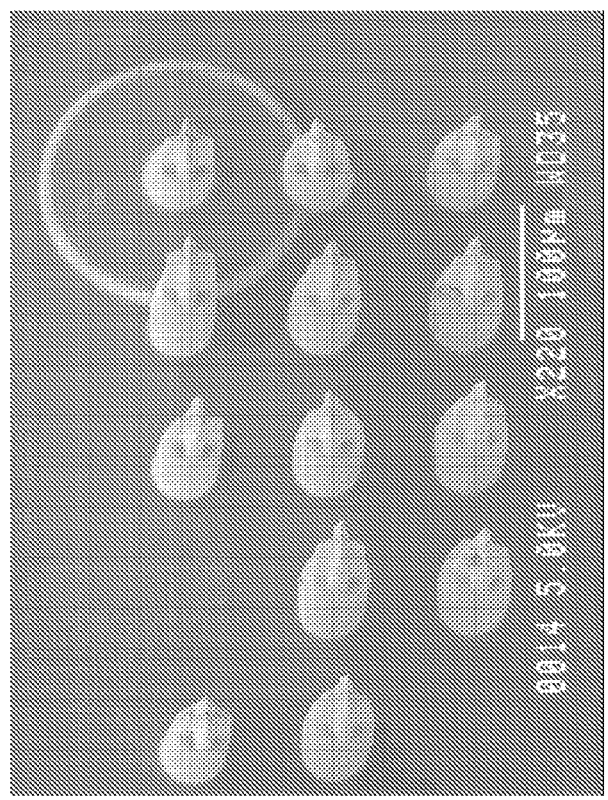
FIG. 13 is a scanning electron micrograph of a molded microneedle array.

Scanning electron micrographs of portions of the resulting microneedle array are shown in FIGS. 13 and 14.

Example 3

The molded microneedle array of Example 2 was used to produce a mold suitable for use in an injection molding process as follows. The molded microneedle array was coated with a silver coating by a vapor deposition process to make a conductive masterform. The masterform was then electroplated to form a 0.09 inch (2.29 mm) thick mold, which was subsequently removed from the masterform. The mold was processed to fit into an injection molding system by cutting it to shape and grinding the backside to be approximately flat. The mold was subsequently cleaned to remove any debris and polymer from the masterform. The mold was then ready for injection molding to produce parts similar to those shown in FIGS. 11 to 14.

Example 4

A microneedle array was prepared as described in Example 1, with the exception that a 300 μm thick layer of uncured epoxy resin, instead of an uncured photosensitive acrylate as in Example 1, was coated onto the silicone wafer. A microneedle array similar to that shown in FIGS. 11 and 12 was prepared. The thus prepared microneedle array was suitable for use in preparing replication tools, as described in Examples 2 and 3.

Example 5

Figure 15:
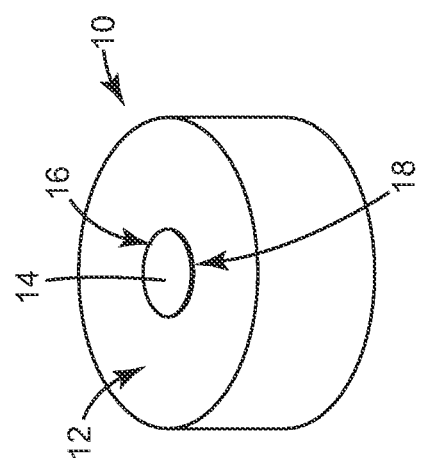
FIG. 15 is a schematic of an aluminum puck used as a substrate

An aluminum "puck" was provided with a machined surface as a substrate for mastering microneedle arrays by two photon polymerization. As illustrated in FIG. 15, aluminum puck 10 had a machined surface 12 which had a raised center portion 14 with a radius 16 around the edge that, when used to create a mold (by electroplating or another molding process) provided a negative relief around the array. This particular geometry was chosen because of the radius around the edge of the raised center portion and because it had a flat spot 18 on part of the raised center portion that could be used as a reference feature for subsequent processes, such as optical inspection of the molded parts produced using a negative tool made from this puck.

The aluminum puck was first prepared by cleaning with ethanol followed by spin coating with the uncured photosensitive acrylate described in Example 1. The photo resist was applied using a traditional spin coater so that the final thickness of the photo resist was about 10 μm. The photo resist was cured using a UV lamp to provide a pre-cured base layer.

Following the formation of the base layer, the puck was coated with a 300 μm thick layer of uncured photosensitive acrylate (described in Example 1) by first applying a die-cut tape that is >300 μm thick around the raised center portion of the puck to provide a "dam" to contain the uncured acrylate resist. A sufficient volume of resist was then poured into the center portion of the puck to form the 300 μm thick layer.

The aluminum puck was then mounted mechanically on the two photon fabrication system. The two-photon fabrication system was then activated to produce an optical signal that was stationary in the vertical position (the fabrication system was not activating the z-control to move the signal in the vertical direction). The signal was used as a detection mechanism to produce a reflection off of the aluminum surface in conjunction with a confocal microscope system such that the only condition that would produce a confocal response would occur when the optical signal was focused on the surface of the aluminum puck. After the surface of the aluminum puck was detected using this system, the puck was moved under the signal to detect if the puck was in the optical plane of the fabrication system. Adjustments were made to a 3-point leveling system that held the carbon vacuum chuck until the puck was contained in the optical plane to less than 500 nm in 3 points that were outside of the planned fabrication area.

The puck was then moved around to detect the outer edges of the raised center portion so that the center position could be calculated. The puck was finally repositioned to the center, and the writing system was moved in the vertical direction (relative to the surface of the puck) to account for the thickness of the pre-cured layer. The fabrication process was started.

Two-photon polymerization was carried out as described in Example 1. A microneedle array was produced that was approximately centered in the raised portion on the puck. After the fabrication process was completed, the microneedle array was developed using MicroChem SU-8 solvent, leaving behind the polymerized structures.

The resultant microneedle array was hexagonal in shape with a total area of about 1 cm$^2$. The needles were arranged in a hexagonal packing arrangement with an average height of 250 μm and a 275 μm tip-to-tip separation between needles.

Three additional masters were produced using this process.

Example 6

The masters of Example 5 were used to produce molds suitable for use in an injecting molding process as follows. The masters were coated in a vacuum system with a thin layer of silver to make conductive masterform arrays. The conductive masterform arrays were then electroplated with nickel to a final electroform thickness of approximately 0.110 inches (2.79 mm). The electroplated parts were then removed from the aluminum pucks and the active surface (the surface that was in contact with the puck) was coated with a thin layer of photo resist by an air-brushing process. This resist protected the surface through subsequent processing. The electroplated parts were processed in a machine shop to grind the backside of the parts to a specific geometry and to cut the parts to fit into an injection molding machine. The parts were then cleaned in a boiling bath of aqueous potassium hydroxide to remove any remaining organic materials, including the protective photo resist and any residual two photon cured structures, leaving the metallic molds ready for injection molding.

Example 7

A circular silicon wafer (10.2 cm (4 inches) in diameter) was provided with a 10 μm thick pre-cured base layer as described in Example 5. The wafer was then coated with a 300 μm thick layer of uncured photosensitive acrylate (as described in Example 1). The backside of the wafer was cleaned with isopropyl alcohol to remove any debris. The wafer was then mounted on a porous carbon vacuum chuck (flatness >1 μm). The two-photon fabrication system was then activated to produce an optical signal that was stationary in the vertical position (the fabrication system was not activating the z-control to move the signal in the vertical direction). The signal was used as a detection mechanism to produce a reflection off of the wafer surface in conjunction with a confocal microscope system such that the only condition that would produce a confocal response would occur when the optical signal was focused on the surface of the wafer. After the surface of the wafer was detected using this system, the wafer was moved under the signal to detect if the wafer was in the optical plane of the fabrication system. Adjustments were made to a 3-point leveling system that held the carbon vacuum chuck until the wafer was contained in the optical plane to less than 500 nm in 4 points that were outside of the planned fabrication area. The writing system was moved in the vertical direction (relative to the surface of the puck) to account for the thickness of the pre-cured layer. Two-photon polymerization was carried out as described in Example 1 to provide a first array. After that array was completed, the wafer was moved in the horizontal direction such that the next array could be written without interfering with the first array. The process was repeated until the last array was completed.

After the fabrication process was completed, the array was developed using MicroChem SU-8 solvent, leaving behind the polymerized structures.

The resulting master contained 8 different microneedle designs. A scanning electron micrograph of a portion of the master is shown in FIG. 16.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:
1. A process for preparing microneedles comprising
(a) providing a photoreactive composition, said photoreactive composition comprising
(1) at least one reactive species that is capable of undergoing an acid- or radical-initiated chemical reaction, and
(2) at least one multiphoton photoinitiator system; and
(b) imagewise exposing at least a portion of said composition to light sufficient to cause simultaneous absorption of at least two photons, thereby inducing at least one acid- or radical-initiated chemical reaction where said composition is exposed to the light, said imagewise exposing being carried out in a pattern that is effective to define at least the surface of a plurality of solid microneedles, wherein the outer surface of the microneedles is characterized by at least one concave area.

2. The process of claim 1, further comprising developing said composition by removing the resulting exposed portion, or the resulting non-exposed portion, of said composition.

3. The process of claim 1, wherein, after imagewise exposing at least a portion of said composition, said process further comprises nonimagewise exposing at least a portion of said composition to light sufficient to react at least a portion of any remaining unreacted photoreactive composition.

4. The process of claim 1 wherein said reactive species is a curable species.

5. The process of claim 1 wherein said reactive species is a non-curable species.

6. The process of claim 1 wherein said multiphoton photoinitiator system comprises photochemically effective amounts of
(a) at least one multiphoton photosensitizer capable of simultaneously absorbing at least two photons;
(b) optionally, at least one electron donor compound different from said multiphoton photosensitizer and capable of donating an electron to an electronic excited state of said photosensitizer; and
(c) at least one photoinitiator that is capable of being photosensitized by accepting an electron from an electronic excited state of said photosensitizer, resulting in the formation of at least one free radical and/or acid.

7. The process of claim 1 wherein said process comprises providing said photoreactive composition on a substrate.

8. The process of claim 1, further comprising a nonimagewise exposure carried out using a one-photon process.

9. A process for preparing a microneedle array, wherein a plurality of microneedles is prepared according to the process of claim 1, and wherein the plurality of microneedles are arranged in a microneedle array.

10. A process for preparing a replication tool, wherein a plurality of microneedles comprising a master is prepared according to the process of claim 1 and the master is used to fabricate a tool for replication.

11. A process for preparing microneedles, wherein a replication tool is prepared according to the process of claim 10, and further comprising the step of molding a polymeric plurality of microneedles with the replication tool.

12. A process for preparing a microneedle array, wherein a plurality of microneedles are prepared according to the process of claim 11, and wherein the plurality of microneedles are arranged in a microneedle array.

13. A microneedle array comprising a plurality of polymeric microneedles, the microneedle array being prepared according to a process comprising:
(a) providing a photoreactive composition, said photoreactive composition comprising:
(1) at least one reactive species that is capable of undergoing an acid- or radical-initiated chemical reaction, and
(2) at least one multiphoton photoinitiator system, wherein the multiphoton photoinitiator system comprises photochemically effective amounts of: (a) at least one multiphoton photosensitizer that is capable of simultaneously absorbing at least two photons and that has a two-photon absorption cross-section greater than that of fluorescein; (b) at least one electron donor compound different from the multiphoton photosensitizer and capable of donating an electron to an electronic excited state of the photosensitizer; and (c) at least one photoinitiator that is capable of being photosensitized by accepting an electron from an electronic excited state of the photosensitizer, resulting in the formation of at least one free radical and/or acid; and
(b) imagewise exposing at least a portion of said composition to light sufficient to cause simultaneous absorption of at least two photons, thereby inducing at least one acid- or radical-initiated chemical reaction where said composition is exposed to the light, said imagewise exposing being carried out in a pattern that is effective to define at least the surface of the plurality of polymeric microneedles, wherein the outer surface of the polymeric microneedles is characterized by at least one concave area.

14. A microneedle array as claimed in claim 13, wherein at least one microneedle has an aspect ratio of between about 2:1 and about 5:1.

15. A microneedle array as claimed in claim 13 wherein at least one microneedle has a flared base.

16. A microneedle array as claimed in claim 13 wherein at least one microneedle comprises:
a base;
a shaft portion extending from the base to a second end distal from the base;
a microblade structure extending from the second end; and
capillary spaces associated with the microblade structure.

17. A microneedle array as claimed in claim 16 wherein the microblade structure comprises a plurality of wing members extending outwardly from a common central axis, each of the plurality of wing members having a corresponding upper edge extending from a common first end at the central axis but terminating at different second ends.

18. A microneedle array as claimed in claim 17 wherein the microblade structure comprises a first wing member having a first upper edge, a second wing member having a second upper edge and a third wing member having a third upper edge, wherein the first, second and third upper edges extend from the common first end and the first, second and third upper edges are substantially coplanar.

19. The microneedle according to claim 18 further comprising a fourth wing member having a fourth upper edge.

20. A microneedle array comprising a plurality of polymeric microneedles comprising photochemically cured compositions, the microneedle array being prepared according to a process comprising:
   (a) providing a photoreactive composition, said photoreactive composition comprising:
      (1) at least one reactive species that is capable of undergoing an acid- or radical-initiated chemical reaction, and
      (2) at least one multiphoton photoinitiator system, wherein the multiphoton photoinitiator system comprises photochemically effective amounts of: (a) at least one multiphoton photosensitizer that is capable of simultaneously absorbing at least two photons and that has a two-photon absorption cross-section greater than that of fluorescein; (b) at least one electron donor compound different from the multiphoton photosensitizer and capable of donating an electron to an electronic excited state of the photosensitizer; and (c) at least one photoinitiator that is capable of being photosensitized by accepting an electron from an electronic excited state of the photosensitizer, resulting in the formation of at least one free radical and/or acid; and
   (b) imagewise exposing at least a portion of said composition to light sufficient to cause simultaneous absorption of at least two photons, thereby inducing at least one acid- or radical-initiated chemical reaction where said composition is exposed to the light, said imagewise exposing being carried out in a pattern that is effective to define at least the surface of the plurality of polymeric microneedles, wherein the outer surface of the polymeric microneedles is characterized by at least one concave area.

* * * * *

UNITED STATES PATENT AND TRADEMARK OFFICE
CERTIFICATE OF CORRECTION

PATENT NO. : 8,858,807 B2  
APPLICATION NO. : 12/293012  
DATED : October 14, 2014  
INVENTOR(S) : Robert Devoe Page 1 of 1

It is certified that error appears in the above-identified patent and that said Letters Patent is hereby corrected as shown below:

SPECIFICATION

Column 6  
Line 23, Delete "11000)," and insert -- 1000), --, therefor.

Column 6  
Line 43, Delete "Morfiex," and insert -- Morflex, --, therefor.

Column 7  
Line 49, Delete "Irgacure" and insert -- Irgacure™ --, therefor.

Column 8  
Line 38-39, Delete "ethyletha- naminium" and insert -- ethylethanaminium --, therefor.

CLAIMS

Column 31  
Claim 19, Delete "The microneedle according to claim" and insert -- "The microneedle array according to claim" --, therefor.

Signed and Sealed this  
Second Day of June, 2015

Michelle K. Lee  
*Director of the United States Patent and Trademark Office*